(12) United States Patent
Verma

(10) Patent No.: US 10,996,218 B2
(45) Date of Patent: *May 4, 2021

(54) METHODS FOR CHEMOTAXIS / REDOX DRIVEN SEPARATION OF X AND Y CHROMOSOME BEARING SPERM AND THEIR INSEMINATION IN GENDER SPECIFIC MENSTRUAL CYCLES

(71) Applicant: OurNextBaby LLC, Livonia, MI (US)

(72) Inventor: Kuldeep C. Verma, Livonia, MI (US)

(73) Assignee: OURNEXTBABY LLC, Livonia, MI (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/008,377

(22) Filed: Jun. 14, 2018

(65) Prior Publication Data

US 2018/0292399 A1    Oct. 11, 2018

Related U.S. Application Data

(63) Continuation-in-part of application No. 14/312,534, filed on Jun. 23, 2014, now Pat. No. 10,018,625, which is a continuation of application No. 12/884,079, filed on Sep. 16, 2010, now Pat. No. 8,759,109, which is a continuation-in-part of application No. 12/401,723, filed on Mar. 11, 2009, now Pat. No. 9,057,720.

(60) Provisional application No. 61/069,008, filed on Mar. 11, 2008, provisional application No. 62/519,797, filed on Jun. 14, 2017.

(51) Int. Cl.

| G01N 33/543 | (2006.01) |
|---|---|
| G01N 33/76 | (2006.01) |
| G01N 33/74 | (2006.01) |
| C12N 5/076 | (2010.01) |
| C12N 5/075 | (2010.01) |

(52) U.S. Cl.
CPC .......... *G01N 33/543* (2013.01); *C12N 5/061* (2013.01); *C12N 5/0609* (2013.01); *G01N 33/743* (2013.01); *G01N 33/76* (2013.01)

(58) Field of Classification Search
None
See application file for complete search history.

(56) References Cited

U.S. PATENT DOCUMENTS

| 3,121,612 A | 2/1964 | Nicholls |
|---|---|---|
| 4,774,339 A | 9/1988 | Haugland |
| 4,810,636 A | 3/1989 | Corey |
| 4,812,409 A | 3/1989 | Babb |
| 4,840,914 A | 6/1989 | Weisberg |
| 5,187,288 A | 2/1993 | Kang |
| 5,274,113 A | 12/1993 | Kang |
| 5,278,782 A | 1/1994 | Nakano |
| 5,433,896 A | 7/1995 | Kang |
| 5,451,526 A | 9/1995 | Cui |
| 5,830,912 A | 11/1998 | Gee |
| 6,207,392 B1 | 3/2001 | Weiss |
| 6,258,540 B1 | 7/2001 | Lo |
| 6,420,182 B1 | 7/2002 | Booth |
| 6,503,198 B1 | 1/2003 | Aronowitz |
| 6,638,415 B1 | 10/2003 | Hodges |
| 6,776,059 B2 | 8/2004 | Kunimune |
| 2003/0087330 A1 | 5/2003 | Glagau |
| 2004/0053335 A1 | 3/2004 | Prusiner |
| 2004/0121420 A1 | 6/2004 | Smith |
| 2004/0259186 A1 | 12/2004 | Paul |
| 2005/0130115 A1* | 6/2005 | Funk .................... A01N 1/0226 435/2 |
| 2006/0096870 A1 | 11/2006 | Sheu |
| 2007/0059774 A1 | 3/2007 | Grisham |
| 2007/0162992 A1 | 7/2007 | Burns |
| 2009/0233321 A1 | 9/2009 | Verma |

(Continued)

FOREIGN PATENT DOCUMENTS

| CN | 1050613 | 4/1991 |
|---|---|---|
| CN | 2309124 | 3/1999 |

(Continued)

OTHER PUBLICATIONS

Agarwal, Ashok, and Shyam SR Allamaneni. "Section 6 Infertility and Recurrent Pregnancy Loss Chapter." Gynecol Obstet Invest 59 (2004): 539-548 (Year: 2004).*

Van Voorhis et al., Cost-Effectiveness of Infertility Treatments, A Cohert Study, Fertility and Sterility, 1997, 830-835. (Year: 1997).*

McRae et al., Metabolic profiling of follicular fluid and plasma from natural cycle in vitro fertilization patients—a pilot study, Assisted Reproduction, 2012; 1449-1457. (Year: 2012).*

Babymed, At Home Artificial Insemination to Get Pregnant—Turkey Baster Method, 2011, retrieved from https://web.archive.org/web/20110711051642/https://www.babymed.com/home-artificial-insemination-get-pregnant-turkey-baster-method on Jul. 16, 2020, 3 pages. (Year: 2011).*

(Continued)

*Primary Examiner* — Andrea S Grossman

(74) *Attorney, Agent, or Firm* — Aurora Consulting LLC; Ashley Sloat

(57) ABSTRACT

The present invention provides a method for determining the gender of a fetus by assaying the sex hormones, evaluating the overall reducing/oxidizing (redox) activity, and/or evaluating the radical scavenging capacity of the maternal urine or other body fluid. The method can be used to determine fetal gender at any time point during pregnancy. The methods of the present invention also provide for a means for pre-conception offspring gender planning by assaying the sex hormones in urine samples, evaluating the overall reducing/oxidizing (redox) activity, and/or evaluating the radical scavenging capacity of the urine or other body fluid from a non-pregnant female. In some embodiments, the methods described herein are used to sort sperm based on an overall reducing/oxidizing environment of follicular fluids, which can then be used for intrauterine insemination.

19 Claims, No Drawings

(56) References Cited

U.S. PATENT DOCUMENTS

| | | | |
|---|---|---|---|
| 2009/0246886 | A1 | 10/2009 | Buck |
| 2014/0302537 | A1* | 10/2014 | Verma .................. G01N 33/743 435/7.92 |

FOREIGN PATENT DOCUMENTS

| | | |
|---|---|---|
| EP | 0184899 | 6/1986 |
| EP | 0186947 | 7/1986 |
| FR | 2441378 | 6/1980 |
| WO | 8001719 | 8/1980 |
| WO | 9003573 | 4/1990 |
| WO | 9839474 | 9/1998 |
| WO | 199922026 | 5/1999 |
| WO | 2002006806 | 1/2002 |
| WO | 2007053191 | 5/2007 |
| WO | 20080607008 | 5/2008 |
| WO | 2008142571 | 11/2008 |
| WO | 2009033212 | 3/2009 |
| WO | 2009056282 | 5/2009 |
| WO | 2009108307 | 9/2009 |

OTHER PUBLICATIONS

Urobiologics, snapshot of website dated Feb. 25, 2007, retrieved from http://web.archive.org/web/20070225030023/http:/www.urobiologics.com, on May 13, 2015.
Urobiologics, snapshot of website dated Feb. 5, 2007 retrieved from http:l/web.archive.org/web/20070205231405/hllp://, www.urobiologics.com/postcon/home.htm, on May 13, 2015.
van de Beek et al., Relationships between sex hormones assessed in amniotic fluid and maternal and umbilical cord serum: What is the best source of information to investigate the effects of fetal hormonal exposure? Hormones and Behavior, 16 (2004) 663-669.
Chen et al., Effect of fetal sex on maternal and fetal human chorionic gonadotropin levels and comparison of their levels in paired umbilical arteries and veins, Proc Nall Sci Counc Repub China B. Feb. 1991;15(1):40-6 (abstract).
Duer et al., Detection of fetal gender differences in maternal serum progesterone concentrations in Asian elephants (*Elephas maximus*), Animal Reproduction Science 97 (2007) 278-283.
Lagona et al., "Multiple testing in fetal gender determination from maternal blood by polymerase chain reaction," Hum. Genet. 1998, vol. 102, No. 6; p. 1.
Jost, "A new look at the mechanisms controlling sex differentiation in mammals," John Hopkins Med. J 1972, vol. 130; p. 38.
Loewit et al., "Determination of fetal sex from maternal testosterone excretion in early pregnancy," Disch. Med. Wschr. 1974, vol. 99; p. 1656.
Intelligender homepage [online]. Retrieved from the Internet Sep. 16, 2009 <URL:http://www.intelligender.com>.
Pigman et al., "The reducing power of human saliva and its component secretions," J Dent Res. 1958, vol. 37, No. 4; pp. 688-696.
Oyawoye et al., "Antioxidants and reactive oxygen species in follicular fluid of women undergoing IVF," Human Reproduction. 2003, vol. 18, No. 11; pp. 2270-2274.
Michaelsson, "A new diazo method for the determination of ascorbic acid in blood plasma", Scand J Clin Lab Inves. 1967, vol. 20; p. 97.
Hughes, "Use of a cation-exchange resin in the determination of urinary ascorbic acid", Analyst. 1964, vol. 89; p. 618.
Nepomnaschy et al., "Urinary hCG patterns during the week following implantation", Human Reproduction. 2008, vol. 23, No. 2; p. 271.
Bowman, "Some of the oxidation-reduction properties of the chorionic gonadotropic hormone", J Biol. Chem. 1940; pp. 293-302.
Gurin et al., "The gonadotropic hormone of urine of pregnancy", J Biol. Chem. 1940, vol. 128; p. 525.

Heteropoly Acid. Wikipedia [online]. Retrieved from the Internet Mar. 9, 2009 <URL:http://en.wikipedia.org/wiki/Heteropoly_acid>.
Scott, "Phosphotungstate: a "universal" (nonspecific) precipitant for polar polymers in acid solution," Journal of Histochemistry and Cytochemistry. 1971, vol. 19, No. 11; p. 689.
Pease, "Polysaccharides & exterior surface of epithelial cells", J Ultrastructure Res. 1966, vol. 15; p. 555.
Oyaizu, "Studies on products of Browning reaction," Japanese J Nutrition. 1986, vol. 44; pp. 307-315.
Huanga et al., "Development and characterization of flexible electrochromic devices based on polyaniline and poly (3,4-ethylenedioxythiophene)-poly(styrene sulfonic acid)," Electrochimica Acta. 2006, vol. 51, No. 26; pp. 5858-5863.
Jones, "Evaluation of immobilized redox indicators as reversible, in situ redox sensors for determining Fe(III)-reducing conditions in environmental samples," Talanta. 2001, vol. 55, No. 4; pp. 699-714.
Prado et al., "A simple and sensitive method for determining reducing sugars in plant tissues", Phytochem. Analysis. 1998, vol. 9, No. 2; pp. 58-62.
Williams et al., "A comparison of mammalian and plant estrogens on vascular reactivity in young and old mice with or without disruption of estrogen receptors," Current Topics in Nutraceutical Res. 2004, vol. 2, No. 4; p. 191.
Oxygen Radical Absorbance Capacity. Wikipedia [online]. Retrieved from the Internet Mar. 2, 2009 <URL:http://en.wikipedia.org/wiki/Oxygen_Radical_Absorbance_Capacity>.
Bahramikia et al., "A comparison of Antioxidant Capacities of ethanol extracts of S. Hortensis and A. Dracunculus leaves," Pharmacology Online. 2008, vol. 2; pp. 694-704.
Steinberg et al., "Chromogenic radical based optical sensor membrane for screening of antioxidant activity," Talanta. 2006, vol. 8; p. 15.
Kohen et al., "Recent advances in chemiluminescence-based immunoassays for steroid hormones," J_ Steriod Biochern. 1987, vol. 27, Nos. 1-3; pp. 71-79.
Lee et al., "Noninvasive in vivo monitoring of methemoglobin formation and reduction with broadband diffuse optical spectroscopy," J Appl. Physiology vol. 100; pp. 615-622.
Yamada et al., "Feasibility and assessment of non-invasive in vivo redox status using electron paramagnetic resonance imaging (EPRI)," Acta Radial. 2002, vol. 43, No. 4; pp. 433-440.
Wang, "Remote electrochemical sensors for monitoring organic and inorganic pollutants," Trends in Anal. Chem. 1997, vol. 16; p. 84.
Balcom et al., "Spatial and temporal visualization of two aqueous iron oxidation-reduction reactions by nuclear magnetic resonance imaging," J Chem Soc. Chem. Comm. 1992; pp. 312-313.
Livesey et al., "Measurement of tissue oxidation-reduction state with carbon-13 nuclear magnetic resonance spectroscopy," Cancer Research. 1989, vol. 49; pp. 1937-1940.
Wu, "Contributions to the chemistry of phosphomolybdic acid, phosphotungstic acid and allied substances," J_ Biol. Chem. 1920, vol. XLIII, No. 1; pp. 189-220.
Polyaniline. Wikipedia [online]. Retrieved from the Internet Mar. 6, 2009 <URL:http://en.wikipedia.org/wiki/Polyaniline>.
Hagens et al., Non-invasive monitoring of oxidative skin stress by ultraweak photon emission measurement. II: biological validation on ultraviolet A-stressed skin, Skin Research and Technology 2008; 14: 112-120.
Miller, "Tissue oxygen tension and the intracellular oxidation-reduction state," National Technical Information Service, 1975.
Dooley et al., "Imaging dynamic redox changes in mammalian cells with GFP indicators," J_ Biol. Chem. 2004, vol. 279, No. 24; pp. 22284-22293.
Supplementary European Search Report dated Mar. 26, 2012.
Boroditsky et al.. "Serum human chorionic gonadotropin and progesterone patterns in the last trimester of pregnancy: relationship to fetal sex." Am J Obstet Gynecol.. 121(2): 238-241 (1975).
Steier et al. "Correlation between fetal sex and human chorionic gonadotropin in peripheral maternal blood and amniotic fluid in second and third trimester normal pregnancies." Acta Obstet Gynecol Scand .. 8(5): 367-371 (1999).

(56) References Cited

OTHER PUBLICATIONS

Yaron et al., "Maternal serum HCG is higher in presence of a female fetus as early as week 3 post-fertilization" Human Reproduction, 17: 485-489 (2002).

International Search Report and Written Opinion for international application No. PCT/US10/49189 dated Jan. 31, 2011.

Wehmann et al. Convenient Radioimmunoassay for human choriogonadotropin without interference by urinary human lutropin. Clinical Chemistry. 27/12.1981. pp. 1997-2001.

Diaz et al. Hydroxylation of salicylate by the in vitro diaphragm: evidence for hydroxyl radical production during fatigue. Journal of Applied Physiology. 75(2). pp. 540-545.

European Search Report issued in corresponding European Application No. 10857389.0 dated Feb. 25, 2014.

Anonymous: Intelligender in the news. Lunatus introduces IntelliGender kit the UAE, Jul. 12, 2010, XP002720139, Retrieved from the Internet: URL:http://www.intelligender.com/intelligender-in-the-news.html [retrived on Feb. 10, 2014] *the whole document.

Bruchez et al., Semiconductor Nanocrystals as Fluorescent Biological Labels. Science, 281, 2013 (1998).

Connor et al. Changes in fruit antioxidant activity among blueberry cultivars during cold-temperature storage. J. Agric. Food Chem. 2002, (50), 893-898.

Riesz et al. Free Radical Generation by Ultrasound in Aqueous and Nonaqueous Solutions. Env. Health Perspectives 1985 (64) 233-252.

Repine et. al. Generation of hydroxyl radical by enzymes, chemicals and human phagocytes in vitro: detection using the anti-inflammatory agent, dimethyl sulfoxide (DMSO). J. Clin. Invest. 1979 (64) 1642-1651.

Shi et. al. Hydroxyl radical generation by electron paramagnetic resonance as a new method to monitor ambient particulate matter composition_ J_ Environ_ Mon it 2003, 5: 550-556.

Weiss et al. Human granulocyte generation of hydroxyl radical. J_ Exp_ Med_ 1978 (147) 316-323.

Shy et al. Sentinel Health Events of Environmental Contamination: A Consensus Statement. Environ_ Health Perspectives 1994, 102(3), 316-317.

Epe et. aL Photolysis of N-Hydroxypyridinethiones: A New Source of Hydroxyl Radicals for the Direct Damage of Cell-Free and Cellular DNA_ Nucleic Acids Res_ 20 1996, 24(9), 1625-1631.

Sadrzsdeh et al. Hemoglobin: A biologic Fenton Reagent J_ Biol. Chem_ 1984, 259(23), 14354-14356.

Puppo et al., Formation of hydroxyl radicals from hydrogen peroxide in the presence of iron_ Biochem J_ 1988 (249), 185-190.

Chevion S. et al. The use of cyclic voltammetry for the evaluation of the antioxidant capacity_ Free Radie_ Biol_ Med_ 2000, 28 (6), 860-870.

Supalkova V., et al. Electroanalysis of plant thiols_ Sensors, 2007 (7), 932-959.

Pohanka et al, Ferric reducing antioxidant power and square wave voltammetry for assay of low molecular weight antioxidants 10 in blood plasma_ Sensors 2009 (9), 9094-9103.

Khabiri et al. Non-invasive monitoring of oxidative skin stress by ultraweak photon emission measurement I: mechanisms of UPE of biological materials_ Skin Research and Technology 14:103-111 (2008).

How to Have a Baby Girl or Boy, www.pickthegenderofyourbaby.com, retrieved Aug. 1, 2011.

Chinese Office Action dated Jan. 5, 2013.

* cited by examiner

METHODS FOR CHEMOTAXIS / REDOX DRIVEN SEPARATION OF X AND Y CHROMOSOME BEARING SPERM AND THEIR INSEMINATION IN GENDER SPECIFIC MENSTRUAL CYCLES

CROSS-REFERENCE TO RELATED APPLICATIONS

This application is a continuation-in-part application of U.S. patent application Ser. No. 14/312,534, filed on Jun. 23, 2014; which is a continuation application of U.S. patent application Ser. No. 12/884,079, filed on Sep. 16, 2010, now issued as U.S. Pat. No. 8,759,109; which is a continuation-in-part of U.S. patent application Ser. No. 12/401,723, filed on Mar. 11, 2009, now issued as U.S. Pat. No. 9,057,720; which claims the benefit under 35 U.S.C. § 119(e) of U.S. Provisional Application No. 61/069,008, filed on Mar. 11, 2008. The disclosure of each of the above applications is incorporated by reference herein in their entirety.

This application also claims the priority benefit under 35 U.S.C. § 119(e) of U.S. Provisional Application No. 62/519,797, filed Jun. 14, 2017, the disclosure of which is herein incorporated by reference in its entirety.

TECHNICAL FIELD

The present invention relates to methods for determining the gender of an unborn child by assaying the sex hormones, evaluating the overall reducing/oxidizing activity, and/or evaluating radical scavenging capacity of the maternal urine. The present invention also relates to methods for pre-conception baby gender planning by assaying the sex hormones, evaluating the overall reducing/oxidizing activity, and/or evaluating radical scavenging capacity of a non-pregnant female's urine prior to conception. The present invention also relates to a method of separating X and Y chromosome containing sperm, without the use of any physical, electric, electronic, magnetic, or centrifugal force, mimicking natural sperm selection in the uterus based on the forces of chemotaxis and redox properties offered by internal sex hormones released by follicular fluid. Such methods described herein may be used in intrauterine insemination (IUI) or in-vitro fertilization (IVF) techniques to increase their success rates.

BACKGROUND

There is a great interest in accurately determining the gender of an unborn child as early as possible. Available techniques are typically performed at late stages of a pregnancy. Ultrasound can be used to determine fetal gender after the 18th week of pregnancy. Polymerase chain reaction (PCR) amplification of Y-specific DNA sequences requires a sample of maternal blood, as well as expensive equipment. PCR can be carried out as early as the 6th week of gestation with an accuracy of only around 80%. Lagona et al. Multiple testing in fetal gender determination from maternal blood by polymerase chain reaction. *Hum. Genet.* 102, 6:1 (1998) Amniocentesis is performed after the 18th week of pregnancy; however, it carries a risk of miscarriage due to its invasiveness. Chorionic Villi Sampling (CVS), conducted between the 10th and 13th week of pregnancy, can also provide accurate information, but again, the procedure is invasive and requires costly equipment.

Alternatively, it is possible to determine the gender of an unborn child by assaying sex hormones. Sex hormones are steroids that play important roles in both normal growth and development. In addition, sex hormones influence the development of sex organs and maintenance of secondary sex characteristics in mammals. Testosterone, the principal male sex hormone, is primarily secreted by the testes of males and, to a much less extent, the ovaries of females. On average, an adult man produces about forty to sixty times more testosterone than an adult woman. Similarly, estrogen functions as the primary female sex hormone and is usually present at significantly higher levels in women than men. The urine from a mother carrying a male fetus is richer in testosterone when compared with the urine from a mother carrying a female fetus. This difference is probably due to the contribution of sex hormones secreted by fetal testes. Jost A. A new Look at the Mechanisms Controlling Sex Differentiation in Mammals. *John Hopkins Med. J.* 130: 38 (1972). Approaches based on a pregnant woman's individual sex hormone levels have been explored to determine fetal gender; however, thus far, they have not resulted in the development of any statistically reliable methods. For example, in one study, antibodies against testosterone were used in a radio-immunoassay to determine the testosterone levels in pregnant mothers' urine. The accuracy of this study with respect to determining fetal gender was low. Loewit et al. Determination of fetal sex from maternal testosterone excretion in early pregnancy. *Dtsch. Med. Wschr.* 99: 1656 (1974).

Urine from pregnant women has been used in various attempts to develop simple and non-invasive tests to determine fetal gender. Most of these procedures exploit simple characteristics of maternal urine such as its pH or the ability to form complexes with aluminum compounds. Consequently, these tests are usually associated with comparatively poor reliability. For example, U.S. Pat. No. 6,420,182 discloses a method for fetal gender detection by assaying the pH of maternal urine after the 12th to 14th week of pregnancy. The test is based on the hypothesis that women bearing female fetuses have acidic urine, but the accuracy of this method is only about 65%. In another assay, a colorimetric test on urine from pregnant women may be performed after the 20th week of pregnancy. U.S. Pat. No. 4,840,914. The accuracy of this test in determining fetal gender was similarly low, only about 60%.

The applicant has noted that assaying multiple sex hormones, evaluating the overall reducing/oxidizing activity, and/or evaluating radical scavenging capacity from urine sample collected near ovulation before pregnancy has significant similarity and correlation with the gender outcome after pregnancy. This suggests that biochemical environment in the uterus existing at the time of conception may be locked and maintained throughout pregnancy. Therefore, evaluation of these parameters before pregnancy would provide reliable methods for pre-conception baby gender planning, as well as provide reliable methods for determining fetal gender after pregnancy. In other words, in addition to X or Y chromosome bearing sperms, the gender of a baby is also influenced by the biochemical environment of the uterus at the time of conception.

Depending upon the processing and assay methods, the hormones which can contribute to the reducing or oxidizing activity of a urine sample are progesterone, testosterone, human chorionic gonadotropin (hCG), and estrogens. For example, estrogens can act as antioxidants, and contribute to the radical scavenging capacity of the urine. The primary hormones directly linked to fetal gender are sex hormones, namely, testosterone and estrogens. The overall reducing/oxidizing activity and/or radical scavenging capacity of the urine sample from a pregnant mother carrying a male fetus is different from that of the urine sample from a pregnant mother carrying a female fetus, thereby allowing for determination of fetal gender.

There is a continuing need to develop a simple, non-invasive and reliable method for determining the gender of an unborn child as early as possible after conception. There is also a need for pre-conception baby gender planning using a simple, non-invasive and reliable technique. Because human and other mammals have similar reproductive biology, these methods may also be of great commercial value to animal breeders.

Further, such redox based pre-conception evaluation of gender specific compatibility of an ovum, post-conception gender determination and relatively more natural sperm sorting techniques may be useful in raising the success rates of artificial fertilization techniques (ART). Current sperm sorting/separation techniques use one or more external forces, including multi-gravitational force, chemical gradient, or electronic pulse etc. Such forces may damage sperm physically or biochemically including DNA damage resulting in less successful ART. For example, Fluorescence Activated Cell Sorting (FACS) uses a cytometer in combination with DNA binding dyes and fluorescence detection. It has been used for detecting minute differences in fluorescence signals originating from a 3.8% difference in total DNA content between X and Y chromosome bearing bovine spermatozoa (G. E. Seidel ˆ D. Garner, Reproduction, 2002, 124,733-743). When the difference in DNA content is detected, an applied electric field sorts the droplet containing the spermatozoa into X and Y chromosome bearing bins. The system can reach up to 25,000 individual spermatozoa per second and is useful in agricultural industries. However, it is known that high shear stress and high voltage cause extensive DNA fragmentation (D. H. Triyoso & T. A. Good, J. Physiol., 1999, 515, 355-365. and M. Stacey, et al, Mutat, Res, Genet, Toxicol, Environ, Mutagen., 2003, 542, 65-75).

Furthermore, current sperm sorting is imperfect, that is, the separation results in a partially enriched fraction containing a 70/30% mixture of X/Y chromosome containing sperm, potentially resulting in the gender of the fetus being other than the parents expected/wanted.

Thus, there is an urgent need of a technique of sorting and effectively separating X and Y chromosome containing sperm, which does not involve any exposure to external physical or biochemical stress. There is also a need to use this approach on natural gender specific conception, either at home or by using intrauterine insemination or in-vitro fertilization. If the technology described herein is used in proper gender specific menstrual cycles, couples, fertile as well as less fertile, can conceive the babies of desired gender, with much higher success rate than existing rates of 10-35% offered by current ARTs.

SUMMARY

It is an object of the present invention to provide a method of determining the gender of an unborn child comprising the steps of: (a) measuring levels of testosterone (T), estrogens (E), progesterone (P) and gonadotropins (G) in a body fluid from a pregnant female; (b) calculating [E−(T+P+G)] as the difference between the level of estrogens (E) and the total levels of testosterone (T), progesterone (P) and gonadotropins (G); and (c) determining the gender of the unborn child to be male if the [E−(T+P+G)] value from step (b) ranges from about 300 to about 1,500, or to be female if the [E−(T+P+G)] value from step (b) ranges from about −10 to about −800. Various steps of the method may be conducted by a human or a machine.

The measurement in step (a) may further comprise a step of contacting the body fluid with testosterone-specific, estrogens-specific, progesterone-specific or gonadotropins-specific antibodies. The level of the sex hormone associated with the antibodies may be determined by ELISA, radioimmunoassay, Western blot, immunoprecipitation, or surface plasmon resonance (SPR) immunoassay. The antibodies can be attached to a solid phase, such as a surface of a cover slip, slide, tube, microtiter well, sheet, chip, reaction tray, strip, membrane, film, fiber, plate, bottle or box. The solid phase may also be a particle, such as a silica, gold, nickel, polystyrene or latex particle. The particle may be a nanoparticle having a diameter between about 0.1 nm and about 100 nm. In one embodiment, the particle comprises a fluorescent compound positioned within the particle; the fluorescent compound of the particle attached to testosterone-specific antibodies, the fluorescent compound of the particle attached to estrogens-specific antibodies, the fluorescent compound of the particle attached to progesterone-specific antibodies, and the fluorescent compound of the particle attached to gonadotropins-specific antibodies are all different.

The levels of testosterone, estrogens, progesterone and gonadotropins may be measured by mass spectrometry, HPLC or multiplex technology.

The method may further comprise a step of attaching the testosterone, estrogens, progesterone and gonadotropins to a solid surface before step (a), such as a surface of a cover slip, slide, tube, microtiter well, sheet, chip, reaction tray, strip, membrane, film, fiber, plate, bottle or box.

The body fluid can be urine, tears, saliva, sweat, blood, plasma, serum, cerebrospinal fluid and amniotic fluid. The body fluid may be obtained during a period ranging from about four days before menstrual due date to about 40 weeks of pregnancy, or during a period ranging from about 4 weeks to about 15 weeks of pregnancy.

The present invention also provides a method of determining the gender of an unborn child comprising the steps of: (a) measuring levels of testosterone (T), estrogens (E), progesterone (P) and gonadotropins (G) in a body fluid from a pregnant female; (b) calculating (E+T)/(P+G) as the ratio of the total levels of estrogens (E) and testosterone (T) to the total levels of progesterone (P) and gonadotropins (G); and (c) determining the gender of the unborn child to be male if the (E+T)/(P+G) ratio from step (b) is greater than about 1.4, or to be female if the (E+T)/(P+G) ratio from step (b) is less than about 1.2.

Further provided in the present invention is a method of determining the gender of an unborn child comprising the steps of: (a) performing hydroxyl radical antioxidant capacity (HORAC) assay on a body fluid from a pregnant female; (b) calculating the HORAC value; and (c) determining the gender of the unborn child to be male if the HORAC value from step (b) is less than about 5000, or to be female if the value from step (b) is greater than about 6000.

Also provided in the present invention is a method of determining the gender of an unborn child comprising the steps of: (a) performing hydroxyl radical antioxidant capacity (HORAC) assay on a body fluid from a pregnant female; (b) measuring levels of testosterone (T) and estrogens (E) in the body fluid, wherein step (b) can be performed before or after step (a); (c) calculating the value of HORAC/(E/T), wherein E/T is the ratio of the level of testosterone to the level of estrogens, and wherein the value of HORAC/(E/T) is the ratio of the HORAC value to the E/T ratio; and, (d)

determining the gender of the unborn child to be male if the value of HORAC/(E/T) from step (c) is less than about 150, or to be female if the value from step (c) is greater than about 200.

The present invention provides for a method of determining the gender of an unborn child comprising the steps of: (a) performing hydroxyl radical antioxidant capacity (HORAC) assay on a body fluid from a pregnant female; (b) measuring levels of testosterone (T), estrogens (E), progesterone (P) and gonadotropins (G) in the body fluid, wherein step (b) can be performed before or after step (a); (c) calculating the value of HORAC/[E−(T+P+G)], wherein [E−(T+P+G)] is the difference between the level of estrogens (E) and the total levels of testosterone (T), progesterone (P) and gonadotropins (G), and wherein the value of HORAC/[E−(T+P+G)] is the ratio of the HORAC value to the [E−(T+P+G)] value; (d) comparing the HORAC/[E−(T+P+G)] value from step (c) with at least one standard; and (e) determining the gender of the unborn child.

The present invention further provides a method of determining the gender of an unborn child comprising the steps of: (a) performing hydroxyl radical antioxidant capacity (HORAC) assay on a body fluid from a pregnant female; (b) measuring levels of testosterone (T), estrogens (E), progesterone (P) and gonadotropins (G) in the body fluid, wherein step (b) can be performed before or after step (a); (c) calculating the value of HORAC/[E+T)/(P+G)] wherein [(E+T)/(P+G)] is the ratio of the total levels of estrogens (E) and testosterone (T) to the total levels of progesterone (P) and gonadotropins (G), and wherein the value of HORAC/[(E+T)(P+G)] is the ratio of the HORAC value to the [(E+T)/(P+G)] value; (d) comparing the HORAC/[E+T)/(P+G)] value from step (c) with at least one standard; and, (e) determining the gender of the unborn child.

Also provided is a method of determining the gender of an unborn child comprising the steps of: (a) contacting a body fluid from a pregnant female with free radicals; (b) measuring free radical scavenging activity of the body fluid; (c) comparing the free radical scavenging activity of the body fluid with at least one standard; and (d) determining the gender of the unborn child. The free radicals may be DPPH (1,1-Diphenyl-2-Picrythydrazyl) radical or GV (2,6-di-tert-butyl-α-(3,5-di-tert-butyl-oxo-2,5-cyclohexadien-1-ylidene)-p-tolyloxy radical. The free radicals may also be hydroxyl radicals or superoxide radicals. The hydroxyl radicals can be generated either internally or externally using heat, irradiation, photolysis, ultrasound, electron paramagnetic resonance, electrolysis, chemical, electrochemical or enzymatic means. The hydroxyl radicals may be generated by Fenton reaction using iron ions, copper ions or titanium dioxide as catalysts.

In one embodiment, the gender of the unborn child is determined to be female if decolorization of DPPH occurs within about 1 minute; the gender of the unborn child is determined to be male if decolorization of DPPH occurs after more than about 1 hour. In another embodiment, the gender of the unborn child is determined to be male if decolorization of DPPH occurs within about 15 minutes; the gender of the unborn child is determined to be female if decolorization of DPPH occurs from about 1 hour to about 24 hours. DPPH may be in a solid form, in a solution, or attached to a solid surface.

The free radical scavenging activity can be measured by methylene blue that is in a solid form, in a solution or attached to a solid surface. In one embodiment, the gender of an unborn child is determined to be female if there is substantially no decolorization of methylene blue; the gender of an unborn child is determined to be male if there is decolorization of methylene blue within about 1 hour.

The present invention further provides for a method of determining the gender of an unborn child comprising the steps of: (a) contacting a body fluid from a pregnant female with a solid surface having antibodies specific to estrogens, antibodies specific to testosterone, antibodies specific to progesterone and antibodies specific to hCG-beta; (b) contacting the solid surface from step (a) with at least one redox indicator; (c) measuring redox activity of the solid surface; (d) comparing the redox activity of the solid surface with at least one standard; and (e) determining the gender of the unborn child. The redox activity may be measured by Ferric reducing/antioxidant power (FRAP) assay or Ferric reducing/antioxidant power using ferric tripyridyltriazine (FRAP-TPTZ) assay.

The present invention also provides for a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating [E−(T+P+G)] as the difference between the level of estrogens (E) and the total levels of testosterone (T), progesterone (P) and gonadotropins (G); and (c) determining the gender specific compatibility of the ovum released in the menstrual cycle to be male if the [E−(T+P+G)] value from step (b) ranges from about 300 to about 1,500, or to be female if the [E−(T+P+G)] value from step (b) ranges from about −10 to about −800.

Further provided in the present invention is a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating (E+T)/(P+G) as the ratio of the total levels of estrogens (E) and testosterone (T) to the total levels of progesterone (P) and gonadotropins (G); and (c) determining the gender specific compatibility of the ovum released in the menstrual cycle to be male if the (E+T)/(P+G) ratio from step (b) is greater than about 1.4, or to be female if the (E+T)/(P+G) ratio from step (b) is less than about 1.2.

Also provided in the present invention is a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) calculating the HORAC value; and (c) determining the gender specific compatibility of the ovum released in the menstrual cycle to be male if the HORAC value from step (b) is less than about 5000, or to be female if the value from step (b) is greater than about 6000.

The present invention provides for a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T) and estrogens (E) in the body fluid, wherein step (b) can be performed before or after step (a); (c) calculating the value of HORAC/(E/T), wherein E/T is the ratio of the level of testosterone to the level of estrogens, and wherein the value of HORAC/(E/T) is the ratio of the HORAC value to the E/T ratio; and (d) determining the gender specific compatibility of the ovum released in the menstrual cycle to be male if the value of HORAC/(E/T) from step (c) is less than about 150, or to be female if the value from step (c) is greater than about 200.

The present invention also provides for a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T), estrogens (E), progesterone (P) and gonadotropins (G) in the body fluid, wherein step (b) can be performed before or after step (a); (c) calculating the value of HORAC/[E−(T+P+G)], wherein [E−(T+P+G)] is the difference between the level of estrogens (E) and the total levels of testosterone (T), progesterone (P) and gonadotropins (G), and wherein the value of HORAC/[E−(T+P+G)] is the ratio of the HORAC value to the [E−(T+P+G)] value; (d) comparing the HORAC/[E−(T+P+G)] value from step (c) with at least one standard; and (e) determining the gender specific compatibility of the ovum released in the menstrual cycle to be male if the HORAC/[E−(T+P+G)] value from step (c) falls within a range of the standard with a male gender specific compatibility, or to be female if the HORAC/[E−(T+P+G)] value from step (c) falls within a range of the standard with a female gender specific compatibility.

The present invention further provides for a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T), estrogens (E), progesterone (P) and gonadotropins (G) in the body fluid, wherein step (b) can be performed before or after step (a); (c) calculating the value of HORAC/[(E+T)/(P+G)] wherein [(E+T)/(P+G)] is the ratio of the total levels of estrogens (E) and testosterone (T) to the total levels of progesterone (P) and gonadotropins (G), and wherein the value of HORAC/[(E+T)(P+G)] is the ratio of the HORAC value to the [(E+T)/(P+G)] value; (d) comparing the HORAC/[(E+T)/(P+G)] value from step (c) with at least one standard; and (e) determining the gender specific compatibility of the ovum released in the menstrual cycle to be male if the HORAC/[(E+T)/(P+G)] value from step (c) falls within a range of the standard with a male gender specific compatibility, or to be female if the HORAC/[(E+T)/(P+G)] value from step (c) falls within a range of the standard with a female gender specific compatibility.

Further provided in the present invention is a method of determining gender specific compatibility of an ovum released in a menstrual cycle for pre-conception baby gender planning comprising the steps of: (a) contacting a body fluid from a non-pregnant female with free radicals; (b) measuring free radical scavenging activity of the body fluid; (c) comparing the free radical scavenging activity of the body fluid with at least one standard; and (d) determining gender specific compatibility of the ovum released in a menstrual cycle.

Further provided in the present invention is a method of determining gender specific compatibility of an ovum released in a menstrual cycle for pre-conception baby gender planning comprising the steps of: (a) contacting a body fluid from a non-pregnant female with a solid surface having antibodies specific to estrogens, antibodies specific to testosterone, antibodies specific to progesterone and antibodies specific to hCG-beta; (b) contacting the solid surface from step (a) with at least one redox indicator; (c) measuring redox activity of the solid surface; (d) comparing the redox activity of the solid surface with at least one standard; and (e) determining the gender specific compatibility of the ovum released in the menstrual cycle.

The present invention provides for a method of conceiving a baby of a desired gender in a female comprising the step of applying to the female a pharmaceutical formulation selected from the group consisting of: (i) a pharmaceutical formulation comprising about 1 ng/ml to about 35 ng/ml estradiol, about 40 ng/ml to about 600 ng/ml estriol, about 0.1 ng/ml to about 35 ng/ml estrone, about 1 ng/ml to about 25 ng/ml testosterone, about 1 ng/ml to about 500 ng/ml progesterone when the desired gender of the baby is male, wherein the [E−(T+P)] value ranges from about 300 to about 1,500, and (ii) a pharmaceutical formulation comprising about 1 ng/ml to about 20 ng/ml estradiol, about 80 ng/ml to about 500 ng/ml estriol, about 1 ng/ml to about 20 ng/ml estrone, about 5 ng/ml to about 80 ng/ml testosterone, about 100 ng/ml to about 1000 ng/ml progesterone when the desired gender of the baby is female, wherein the [E−(T+P)] value ranges from about −10 to about −800. The pharmaceutical formulation may be in the form of a gel, a solution, a cream, a lotion, an ointment, a foam or a paste.

DETAILED DESCRIPTION

The present invention provides methods for determining the gender of an unborn child as well as preconception fetal gender planning by assaying various sex hormones, evaluating the overall redox activity, and/or evaluating radical scavenging capacity of the maternal urine or a non-pregnant female's urine. The methods may be conducted in other body fluids such as tears and cerebrospinal fluid. The method can be used to determine fetal gender at any time point during the entire pregnancy, i.e., from about four days before menstrual due date to about 40 weeks of pregnancy. In one embodiment, the body fluid is obtained from a pregnant female between the 4th week and 15th week of pregnancy. In order to improve accuracy of the results, the body fluid may be processed before assaying. Processing may involve aging the body fluid, or purification of various fractions. For example, processing can comprise aging the urine by storing it at ambient temperature (e.g., approximately, 20-30° C.) for a defined period of time, e.g., 1-4 weeks, treating the urine by physical, chemical or biochemical means to accelerate the aging process, and/or removing various urinary components by physical, chemical or biochemical means. Repeated analysis of urine samples obtained from the same test subject at different time points in the pregnancy appears to improve the accuracy of the analytical results. For example, if three urine samples are analyzed, we have found that the accuracy of the results approaches 100%.

The methods of the present invention also provide for a means for pre-conception baby gender planning by assaying the sex hormones, evaluating the overall redox activity, and/or evaluating radical scavenging capacity of a non-pregnant female's urine or other body fluid. The body fluid may be assayed at anytime during a menstrual cycle, but preferably is assayed around the time of ovulation or middle of the menstrual cycle. Without being limited to any specific physiological mechanism, it is believed that ovulation generates at least two types of uterine environments during alternate menstrual cycles, presumably due to the release of two different types of ova. One type of ovum is associated with uterine environments to be compatible with fertilization by a Y chromosome-bearing sperm to produce a male fetus, whereas the other type of ovum is associated with uterine environments to be compatible with fertilization by an X chromosome-bearing sperm to produce a female fetus. The fertilization rate for a sperm and an ovum in incompatible environments is very low. We have found that sex hormone levels, the overall redox activity, and/or radical scavenging capacity of a urine sample correlate with the gender specific compatibility of the ovum being released during a particular menstrual cycle. Therefore, assaying sex hormone levels, the overall redox activity, and/or radical scavenging capacity of a non-pregnant female's urine will help a couple conceive a baby of a desired gender.

The methods of the present invention may encompass assaying any suitable body fluid, including urine, tears, saliva, sweat, blood, plasma, serum, cerebrospinal fluid and amniotic fluid. Pigman et al. The reducing power of human saliva and its component secretions. *J. Dent Res.* 37(4): 688-696 (1958). Oyawoye et al. Antioxidants and reactive oxygen species in follicular fluid of women undergoing IVF. *Human Reproduction.* 18 (11): 2270-2274 (2003).

The term "overall redox activity" or "redox activity" of a body fluid refers to the net redox activity (including antioxidant activity and/or radical scavenging capacity) of a body fluid as a whole, although various components of the body fluid may exhibit different redox activities individually. The overall redox activity of a body fluid such as urine depends not only on the composition of the urine, but also, on how the sample is processed before assaying, as well as on the assay conditions. For example, the body fluid may be "aged" for at least about 1 week at room temperature ranging from about 20° C. to about 30° C. before assaying. The body fluid may also be aged for longer periods of time such as about 1, 2, 3, 4, 5, 6, 7, 8, 9, 10, 1 and 12 months. The body fluid may be aged at room temperature for a period of time ranging from about 1 week to about 52 weeks prior to assaying. Aging of the urine sample can range from as long as 1 year to about 5 years, but longer periods may also be appropriate. Other suitable chemical, biochemical or physical treatments may also be used to process the urine before assaying.

The term "fetal gender related characteristics" refers to (i) the evaluation of the type of uterine environment and compatibility of ovum released in a particular menstrual cycle before pregnancy, and (ii) the determination of sex of the fetus after pregnancy. Accordingly, "male gender related characteristics" refers to (i) a uterine environment and/or ovum released in a particular menstrual cycle compatible to fertilize a Y chromosome-bearing sperm before pregnancy, and (ii) a male unborn baby. Similarly, "female gender related characteristics" refers to (i) a uterine environment and/or ovum released in a particular menstrual cycle compatible to fertilize an X chromosome-bearing sperm before pregnancy, and (ii) a female unborn baby.

The term "gender specific compatibility" refers to the compatibility of an ovum (or uterus) for fertilization by either a Y chromosome-bearing sperm to produce a male fetus, or by an X chromosome-bearing sperm to produce a female fetus. When an ovum (or uterus) is compatible with fertilization by a Y chromosome-bearing sperm to produce a male fetus, the gender specific compatibility of the ovum (or uterus) is male; when an ovum (or uterus) is compatible with fertilization by an X chromosome-bearing sperm to produce a female fetus, the gender specific compatibility of the ovum (or uterus) is female.

Estrogens include, but are not limited to, estradiol, estriol, estrone, their metabolites and derivatives. Sex hormones include, but are not limited to, estrogens, androgens, progestogens, hCG, follicular stimulating hormone, leutenising hormones, glycoproteins, as well as their metabolites, breakdown products and derivatives. Androgens may include testosterone, dihydrotestosterone, dehydroepiandrosterone and androstenedione. Progestogens include all steroids with a pregnane skeleton, such as progesterone.

The present invention provides a method of determining the gender of an unborn child comprising the steps of: (a) measuring levels of testosterone (T), estrogens (E), progesterone (P) and gonadotropins (G) in a body fluid from a pregnant female; (b) calculating [E−(T+P+G)] as the difference between the level of estrogens (E) and the total levels of testosterone (T), progesterone (P) and gonadotropins (G); (c) comparing the [E−(T+P+G)] value from step (b) with at least one standard; and (d) determining the gender of the unborn child. The sex hormones, such as testosterone, estrogens, progesterone and gonadotropins, may be attached to a solid surface before step (a).

In one embodiment, there is provided a method of determining the gender of an unborn child comprising the steps of: (a) measuring levels of testosterone (T), estrogens (E), progesterone (P) and gonadotropins (G) in a body fluid from a pregnant female; (b) calculating [E−(T+P+G)] as the difference between the level of estrogens (E) and the total levels of testosterone (T), progesterone (P) and gonadotropins (G); and (c) determining the gender of the unborn child to be male if the [E−(T+P+G)] value from step (b) ranges from about 300 to about 1,500, or to be female if the [E−(T+P+G)] value from step (b) ranges from about −10 to about −800.

Because the measured levels of the sex hormones may depend on the particular reagents and method that is used to measure the sex hormone levels, the mathematical relationship of the various sex hormones in the body fluid from a test subject may be compared with that of a standard, i.e., a body fluid from a pregnant female where the sex of the fetus is known, to determine the gender of the fetus carried by the test subject. Alternatively, the mathematical relationship of the various sex hormones in the body fluid from a test subject is compared with the mathematical relationship of the various sex hormones of the body fluid samples from pregnant females where the sexes of the fetuses are known, to determine the gender of the fetus carried by the test subject. Similarly, for pre-conception methods, the mathematical relationship of the various sex hormones of the body fluid from a test subject is compared with that of a standard, i.e., body fluid from a non-pregnant female where the gender specific compatibility of the ovum the female generated is known, to determine the gender specific compatibility of the ovum produced by the test subject. Alternatively, the mathematical relationship of the various sex hormones of the body fluid from a test subject is compared with the mathematical relationship of the various sex hormones of the body fluid samples from non-pregnant females where the gender specific compatibilities of the ova the females generated are known, to determine the gender specific compatibility of the ovum produced by the test subject. The mathematical relationship of the various sex hormones of the standard may be determined using any method encompassed by this invention. One standard may be used in the present invention. Alternatively, more than one standard may be used. The standard may be at least one body fluid sample from one female, or may be at least one body fluid sample from more than one female where the sex of the fetus or the gender specific compatibility of the ovum is known. Thus, the value of the standard can be a range corresponding either to a female fetus (or female gender specific compatibility of the ovum) or a male fetus (or male gender specific compatibility of the ovum). Alternatively, more than one body fluid sample from one female, or at least one body fluid sample from more than one female, can be pooled, and the standard value determined.

The level of a sex hormone can be measured by any suitable method known to those skilled in the art. For example, the level of a sex hormone can be measured by specific antibodies or antigen-binding fragments. The measurement may thus comprise a step of contacting the body fluid with, for example, testosterone-specific, estrogens-specific, progesterone-specific and/or gonadotropins-specific antibodies.

A detectable label may be conjugated to the antibody or antigen-binding fragment. A detectable label may be conjugated to a primary antibody and/or a secondary antibody. Exemplary detectable labels include a radioisotope, a fluorophore, a luminescent molecule, an enzyme, a biotin moiety, an epitope tag, a dye molecule, and a molecule capable of activating a chemiluminescent substrate. Exemplary enzyme labels include phosphatases (such as, alkaline phosphatase (ALP)) and peroxidases (e.g., horseradish peroxidase (HRP)). These and others will be apparent to one of ordinary skill in the art. WO2009108307.

The level of the sex hormone associated with the antibodies may be determined by any suitable assay, such as enzyme-linked immunosorbent assay (ELISA), immunoassay (including enzyme immunoassay), radioimmunoassay, immunoradiometric assay, immunochemiluminescent assay, Western blot, immunoprecipitation, and surface plasmon resonance (SPR) immunoassay. See, for example, WO 2009033212. In one embodiment, testosterone enzyme immunoassay test kit and estradiol (E2) enzyme immunoassay test kit from BioCheck, Inc. may be used to determine testosterone and estradiol levels. Levels of different sex hormones can be measured by the same method or by different methods. WO 2008067008 discloses using SPR technology to simultaneously and quantitatively measure the concentrations of different sex hormones in a sample.

When level of the sex hormone is measured by specific antibodies, the antibodies may be provided in a solution or may be attached to a solid phase. The solid phase may be a particle, bead, cover slip, slide, tube, microtiter well, sheet, chip, reaction tray, strip, membrane, film, fiber, plate, bottle, box, or any other shape/material suitable for the present invention. The solid surface may be of any material or shape capable of supporting chemical reactions.

When the solid phase is a particle, the particle may be a microparticle or nanoparticle. The diameter of the particle may be from about 0.1 nm to about 100 mm, from about 10 nm to about 50 mm, from about 100 nm to about 30 mm, from about 500 nm to about 20 mm, from about 0.1 nm to about 100 nm, or from about 700 nm to about 10 mm. The solid phase can consist of natural, semi-synthetic or synthetic materials. The solid phase can be made of biodegradable and/or non-biodegradable materials. Non-biodegradable materials include, but are not limited to, silica, latex, glass, quartz, metal (e.g., nickel, gold, colloidal gold), mica, plastic, derivatized plastic, ceramic, carbon, bentonite, alumina, borosilicate, zeolites, natural or synthetic composites of redox sensitive materials like iron, copper, chromium, manganese, tungsten, molybdenum, vanadium, arsenic, germanium, or combinations thereof. The carrier matrix can be made of polyester, polycarbonate, polysulfone, polyvinyl chloride, polyethylene, polypropylene, poly(N-vinyl pyrrolidone), poly(methyl methacrylate), poly(vinyl alcohol), poly(acrylic acid), polyacrylamide, poly(ethylene-co-vinyl acetate), poly(methacrylic acid), and combinations thereof. Biodegradable materials include, but are not limited to, starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. European Patent Application Nos. 0184899 and 0186947. The solid phase may contain polystyrene, polysuflone, polyurethane, and polytetrafluoroethylene (PTFE), polyacrylate and their derivatives, copolymers (e.g. Eupergit and Dynospheres), protein (such as gelatin), polysaccharides (such as dextran, agarose, cellulose, nitrocellulose), acrylic, or mixtures thereof.

The solid phase may also comprise additive agent that provides additional properties to the particle. Such additives include magnetic material, or a fluorescent compound.

In certain embodiments, the antibodies are attached to a particle having a fluorescent compound positioned within or on the surface of the particle. The antibodies may be attached directly to the fluorescent compound. Antibodies with different specificity may be associated with fluorescent compounds having emission spectra distinguishable from each other, allowing for binding of different sex hormones to the particle and for different sex hormones to be distinguished. Labeling multiple antibodies with different fluorescent compounds allows measurement of multiple hormones simultaneously. For example, the fluorescent compounds attached to testosterone-specific antibodies, estrogens-specific antibodies, progesterone-specific antibodies and gonadotropins-specific antibodies may all be different.

In certain embodiments, there are a fluorescent compound positioned within a particle attached to specific antibodies, where the specificities of the antibodies attached to one particle are the same. For example, a particle only contains antibodies specific to testosterone, estrogens, progesterone or gonadotropins. The fluorescent compound of the particle attached to testosterone-specific antibodies, the fluorescent compound of the particle attached to estrogens-specific antibodies, the fluorescent compound of the particle attached to progesterone-specific antibodies, and the fluorescent compound of the particle attached to gonadotropins-specific antibodies are all different.

The fluorescent compounds that may be used in this invention can cover the entire UV-V is to near-IR absorption and emission spectrum. Any known fluorescent compound may be used, such as fluorescent organic compound, dyes, pigments, or combinations thereof. A wide variety of suitable fluorescent dyes are known, see, for example, Molecular Probes Handbook of Fluorescent Probes and Research Chemicals, 6th ed., R. P. Haugland, ed. (1996). A typical fluorophore is, for example, a fluorescent aromatic or heteroaromatic compound such as is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof), and like compounds, see for example U.S. Pat. Nos. 5,830,912, 4,774,339, 5,187,288, 5,248,782, 5,274,113, 5,433,896, 4,810,636 and 4,812,409.

Various kinds of fluorophores are known in the art, including, but not limited to, fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red, LightCycler-Red 640, Light-Cycler Red 705, tetramethylrhodamine (TMR), rhodamine, rhodamine derivative (ROX), hexachlorofluorescein (HEX), Cy5, Cy5.5 (also known as Cy5++), Cy2, rhodamine 6G (R6G), the rhodamine derivative JA133, Alexa Fluorescent Dyes (such as Alexa Fluor 488, Alexa Fluor 546, Alexa Fluor 633, Alexa Fluor 555, and Alexa Fluor 647), 4',6-diamidino-2-phenylindole (DAPI), Propidium iodide, AMCA, Spectrum Green, Spectrum Orange, Spectrum Aqua, Lissamine, and fluorescent transition metal complexes, such as europium. Fluorophores that can be used also include fluorescent proteins, such as GFP (green fluorescent protein), enhanced GFP (EGFP), blue fluorescent protein and derivatives (BFP, EBFP, EBFP2, Azurite, mKalamal), cyan fluorescent protein and derivatives (CFP, ECFP, Cerulean, CyPet) and yellow fluorescent protein and derivatives (YFP, Citrine, Venus, YPet). WO2008142571, WO2009056282, WO9922026.

The particles of the present invention may exhibit intrinsic fluorescence. U.S. Pat. No. 6,207,392. Bruchez et al., Semiconductor Nanocrystals as Fluorescent Biological Labels. *Science,* 281, 2013 (1998). Particles that are able to bind one type of sex hormone may have same or similar diameter, which can be different from the diameter of the particles binding to a different type of sex hormone. Particles having different diameters may have different emission spectra distinguishable from each other. For example, nanoparticles of different diameters may exhibit different optical color. In one embodiment, various antibodies for different sex hormones are attached to a solid phase. After the body fluid, e.g., urine, is added to the solid phase, sex hormones will bind to their specific antibodies attached to the solid phase. When the antibody-linked particles are added to the surface of the solid phase, the intensity of the emission of the particles with a specific emission spectrum will correspond to the level of a sex hormone. Accordingly, the fetal gender related characteristics such as the gender of an unborn baby can be determined by the overall emission spectrum or the overall optical color of the solid phase. Alternatively, the antibodies attached to the particle may be conjugated with at least one redox indicator. The fetal gender related characteristics such as the gender of an unborn baby can then be determined by the overall redox activity of the solid phase.

In another embodiment, the body fluid, e.g., urine, is added to the particles. Different sex hormones in the body fluid will then attach or be adsorbed to particles exhibiting different spectral or optical properties (for example, exhibiting different colors). The particles with the attached (or adsorbed) sex hormones are added to a solid phase to which various antibodies for different sex hormones are attached. Then, the overall color exhibited by such a solid surface can be used to evaluate fetal gender related characteristics. Alternatively, the antibodies attached to the particle may be conjugated with at least one redox indicator, and the overall redox activity of the solid phase can be determined by reacting such a solid surface with a redox indicator, thereby revealing fetal gender related characteristics.

The level of the sex hormone may be measured by any other suitable technique known to a skilled artisan. The techniques include, but are not limited to, mass spectrometry (MS), high performance liquid chromatography (HPLC), gas chromatography (GC), GC-MS, affinity chromatography, ion exchange chromatography, size exclusion chromatography, and reversed-phase chromatography, nuclear magnetic resonance (NMR) spectroscopy, infrared spectroscopy (IR), thin layer chromatography (TLC), and multiplex array technology.

The levels of different sex hormones, such as testosterone, estrogens, progesterone and gonadotropins, may be measured in separate assays, or may be measured simultaneously or sequentially in one assay.

The present invention provides a method of determining the gender of an unborn child comprising the steps of: (a) measuring levels of testosterone (T), estrogens (E), progesterone (P) and gonadotropins (G) in a body fluid from a pregnant female; (b) calculating (E+T)/(P+G) as the ratio of the total levels of estrogens (E) and testosterone (T) to the total levels of progesterone (P) and gonadotropins (G); and, (c) comparing the ratio (E+T)/(P+G) from step (b) with at least one standard to determine the gender of the unborn child.

In one embodiment, there is provided a method of determining the gender of an unborn child comprising the steps of: (a) measuring levels of testosterone (T), estrogens (E), progesterone (P) and gonadotropins (G) in a body fluid from a pregnant female; (b) calculating (E+T)/(P+G) as the ratio of the total levels of estrogens (E) and testosterone (T) to the total levels of progesterone (P) and gonadotropins (G); and (c) determining the gender of the unborn child to be male if the (E+T)/(P+G) ratio from step (b) is greater than about 1.4, or to be female if the (E+T)/(P+G) ratio from step (b) is less than about 1.2.

The present invention provides a method for determining the gender of an unborn child comprising the steps of: (a) contacting a body fluid from a pregnant female with at least one redox indicator; (b) measuring redox activity of the body fluid; and, (c) comparing the redox activity of the body fluid with at least one standard to determine the gender of the unborn child.

Because the ability of the body fluid to reduce or oxidize a reagent will depend on the particular reagent (reducing agent or oxidizing agent) that is used to measure reduction or oxidation, the redox activity of the body fluid from a test subject is compared with the redox activity of a standard, i.e., the body fluid from a pregnant female where the sex of the fetus is known, to determine the gender of the fetus carried by the test subject. Alternatively, the redox activity of the body fluid from a test subject is compared with the redox activity of the body fluid samples from pregnant females where the sexes of the fetuses are known, to determine the gender of the fetus carried by the test subject. Similarly, for pre-conception methods, the redox activity of the body fluid from a test subject is compared with the redox activity of a standard, i.e., body fluid from a non-pregnant female where the gender specific compatibility of the ovum the female generated is known, to determine the gender specific compatibility of the ovum produced by the test subject. Alternatively, the redox activity of the body fluid from a test subject is compared with the redox activity of the body fluid samples from non-pregnant females where the gender specific compatibilities of the ova the females generated are known, to determine the gender specific compatibility of the ovum produced by the test subject. The redox activity of the standard may be determined using any method encompassed by this invention. One standard may be used in the present invention. Alternatively, more than one standard may be used.

The overall redox activity or the mathematical relationship of the various sex hormones of the body fluid such as urine may depend not only on the composition of the urine, but also, on how the sample is processed before assaying, as well as on the assay conditions. For example, if the urine sample is not aged or is assayed under mild conditions (see description below), the overall redox activity of the urine correlates with its in vivo overall redox activity. Namely, the urine from a female carrying a female fetus will have a comparatively higher overall reducing activity (or antioxidant activity, or radical scavenging activity) than urine from a female carrying a male fetus.

A similar observation has been made for pre-conception assays. Namely, if the urine sample is not aged or is assayed under mild conditions, the urine sample of a non-pregnant female carrying an ovum compatible with fertilization by an X chromosome-bearing sperm will have a comparatively higher reducing activity (or antioxidant activity, or radical scavenging activity) than urine from a non-pregnant female carrying an ovum compatible with fertilization by a Y chromosome-bearing sperm.

In contrast, if the urine sample is allowed to age and/or is assayed under harsh conditions (see description below), the urine would exhibit an overall redox activity different from its activity in vivo. Namely, the urine from a female carrying a male fetus will have a comparatively higher overall reducing activity than urine from a female carrying a female fetus.

Likewise, with pre-conception testing, if the urine sample is assayed under harsh conditions, the urine sample of a non-pregnant female carrying an ovum compatible with fertilization by a Y chromosome-bearing sperm will have a comparatively higher reducing activity than urine from a non-pregnant female carrying an ovum compatible with fertilization by an X chromosome-bearing sperm. See Table 1 for the redox activities of the urine samples under different processing and assay conditions.

There are a number of reducing or oxidizing compounds present in the urine that may interfere with the assays of the present invention. Therefore, the urine may be processed to remove these compounds before assaying the redox activity. Interfering reducing and oxidizing agents include urea, thiourea, creatine, uric acid, ascorbic acid, glucose, glucuronic acid, bilirubin, creatinine, porphyrins and related pigments, nitrites, sulfites, bisulfites, hyposulfites, pyrosulfites, sulfates oxyacids (such as sulfurous acid, bisulfurous acid, hyposulfurous acid, pyrosulfurous acid), urobilinogen, hemoglobin or other interfering proteins, and leucocytes. Interfering agents can be removed by treatment with enzymes including ascorbic acid oxidase, glucose oxidase, urease and uricase. Glucose may be removed by an anion exchange resin such as Amberlite-4B or alumina. Interfering agents may also include progesterone, its derivatives and/or metabolites, which may be removed by adsorbents such as mica and highly oriented pyrolytic graphite, or by antibodies against progesterone, its derivatives and/or metabolites. Ascorbic acid can be removed by resin extraction, diazotized 4-nitroaniline-2,5-dimethoxyaniline, ascorbic acid oxidase, lead acetate, iodate, and/or their combinations. Michaelson. *Scand J Clin Lab Inves* 20: 97 (1967). Hughes. *Analyst,* 89:618 (1964).

Chemical, biochemical or physical treatments may also be used to remove the interfering reducing and/or oxidizing compounds before assaying. The treatments may include extraction, purification, adsorption, and treatments by mineral acids, enzymes or microwaving. The body fluid may also be processed by treatment with adsorbants and/or precipitants. Adsorbants may be selected from the group consisting of talc, silica-based particles such as silica gel, alumina, florisil, charcoal, kaolin, concanavaline A and its

TABLE 1

| | | Testosterone:Estrogens Ratio | Urine not aged or assayed under mild conditions | Urine aged or assayed under harsh conditions |
|---|---|---|---|---|
| Post-conception | Male Fetus | Greater than about 1 | Comparatively higher overall oxidizing activity | Comparatively higher overall reducing (or antioxidant) activity |
| | Female Fetus | Less than about 1 | Comparatively higher overall reducing (or antioxidant) activity | Comparatively higher overall oxidizing activity |
| Pre-conception | Ovum compatible with Y chromosome-bearing sperm | Greater than about 1 | Comparatively higher overall oxidizing activity | Comparatively higher overall reducing (or antioxidant) activity |
| | Ovum compatible with X chromosome-bearing sperm | Less than about 1 | Comparatively higher overall reducing (or antioxidant) activity | Comparatively higher overall oxidizing activity |

The term "mild condition" refers to processing of the body fluid prior to assaying and assaying of the body fluid by treatment at temperatures lower than about 21° C. or treatment with mild chemicals, such as talc, alumina, extraction using organic solvents, solid phase extraction (SPE) chromatography or phosphotungstic acid (PTA). The term "harsh condition" refers to processing of the body fluid prior to assaying or assaying of the body fluid by treatment at temperatures greater than about 21° C. or treatment by harsh chemicals, such as strong acids, strong alkalis, trichloroacetic acid and strong oxidizing agents. Strong oxidizing agents include potassium ferricyanide in the ferric reducing/antioxidant power (FRAP) assay. The particular condition of the processing of the body fluid prior to assaying or assaying of the body fluid can be determined by one of ordinary skill in the art without undue experimentation.

conjugates, calcium phosphate, calcium hydroxide, calcium chloride, Cetyltrimethyl ammonium bromide, lectin specific to the carbohydrate portion of urinary gonadotropins or glycoproteins, protein or glycoprotein hydrolyzing enzymes, glassfiber filter, ion exchange resins, affinity ligands, extraction using organic solvents, solid phase extractants, size exclusion sieves, and reverse phase chromatographic materials. Precipitants may be salts of heavy metals, which are selected from the group consisting of barium, lead, molybdenum and tungsten. Precipitants may comprise barium chloride, barium hydroxide mixed with zinc chloride, mercuric chloride, lead acetate and their mixtures. Precipitants may also comprise ammonium sulphate, dextran, acetonitrile, chloroform, sodium hydroxide, trichloroacetic acid, potassium iodate and their mixtures. One or more than one adsorbant or precipitant may be used; in addition, adsorbant and precipitant may be used in combination. Adsorbants or precipitants may be used to adsorb or retain the interfering reducing or oxidizing agents. Alternatively, adsorbants or precipitants may be used to adsorb or retain desired urinary fraction, which may later be eluted with appropriate solvents for assaying.

When the urine sample is allowed to age, most of the interfering reducing or oxidizing components appear to be eliminated. In one embodiment, the urine sample is first processed by physical, chemical or biochemical means to accelerate the aging process. The urine sample is then treated by other chemical, physical or biochemical means to obtain a purified or partially purified fraction, followed by assaying the overall redox activity of the urine sample under harsh conditions.

Prior to assaying, insoluble components may be removed from the body fluid, for example, by filtration or centrifugation. A non-interfering pH indicator may also be added prior to assaying. The pH of the body fluid may be adjusted.

The primary hormones directly linked to fetal gender are sex hormones. The ratio of testosterone to estrogens is greater than about 1.0 in the urine from a mother carrying a male fetus, whereas the ratio of testosterone to estrogens is less than about 1.0 in the urine from a mother carrying a female fetus. The same may be true for midcycle urine samples from non-pregnant women. Sex hormones, including testosterone and estrogen, are excreted in urine as their glucuronides associated with large glycoproteins such as human chorionic gonadotropin (hCG), sex hormone-binding globulin, as well as other glycoproteins. In freshly voided urine, sex hormones maintain their association with these large molecules. Without being limited to any specific physiological mechanism, it is believed that the overall redox activity of a urine sample assayed under mild conditions or without aging is the net redox activity of various urinary complexes which comprise sex hormones and large molecules such as hCG, sex hormone-binding globulin, as well as other glycoproteins.

When urine is assayed under harsh conditions, the hormones which can contribute to the reducing activity of a urine sample are progesterone, testosterone and human chorionic gonadotropin (hCG) and or its degradation byproducts, whereas estrogens can contribute to the oxidizing activity of the urine. hCG is a glycoprotein hormone specifically produced in pregnancy that is secreted by the embryo soon after conception and later by the placenta. hCG's major role is to maintain progesterone production that is critical for maintaining a pregnancy in humans. Many currently available early pregnancy tests are based on the detection or measurement of hCG in the blood or urine. The urine or blood level of hCG itself does not correlate with the gender of the fetus. hCG exhibits reducing activity. Nepomnaschy et al. *Human Reproduction.* 2008. 23(2): 271. Under harsh assay conditions, if a urine sample is from a female carrying a male fetus, there is no other stronger reducing agent (or antioxidant) in the urine sample that is able to protect hCG from being oxidized by urinary oxidizing agents. Bowman D. E. *J. Biol. Chem.* 1940, p 293-302. Gurin et al. *J. Biol. Chem.* 1940. 128: 525. As a result, hCG is oxidized and subsequently degraded to its constituents including galactoses and hexoamines, both of which have much stronger reducing activities than hCG. As a result, galactoses and hexoamines contribute to a comparatively higher overall reducing activity of the urine from a female carrying a male fetus in comparison with urine from a female carrying a female fetus. In contrast, in a freshly voided urine sample without aging or under mild assay conditions, if a urine sample is from a female carrying a female fetus, a relatively higher concentration of estrogen in the urine sample is able to protect hCG from oxidizing agents by interacting with the oxidizing agents. As a result, hCG is not oxidized or degraded to the same extent. Rather, hCG is degraded at a much slower rate in comparison to hCG in the urine sample from a female carrying a male fetus. Therefore, after aging or under harsh conditions, the urine from a female carrying a male fetus would exhibit a higher overall reducing activity than the urine from a female carrying a female fetus.

In samples from non-pregnant women, hCG may play a less significant role, whereas other glycoproteins like FSH and LH may be more important.

Sex hormones are excreted in urine as their glucuronide conjugates. As the urine sample is aged, glucuronide conjugates are hydrolyzed and free sex hormones released. To facilitate release of the free sex hormones from their glucuronide conjugates, a urine sample may be treated with the enzyme β-glucuronidases. β-glucuronidases purified from various sources can be used, including bovine liver, snail *Helix pomatia* and *E. coli*. In one embodiment, the urine sample is treated with β-glucuronidases from *E. coli* for 24 hours. In another embodiment, the urine sample is treated with *E. coli* β-glucuronidases for 2 hours.

The urine sample may also be treated by a mineral acid to facilitate release of the free sex hormones from their glucuronide conjugates. The mineral acid may be hydrochloric acid or sulfuric acid. The yield of hydrolysis is determined by the property and concentration of the acid. In one embodiment, a complete hydrolysis of the sex hormone glucuronide conjugates is achieved by treating a urine sample with 3 M sulfuric acid at 37° C. for 24 hours.

The redox potential of the body fluid may also be assayed. Redox potential may be determined by measuring the potential difference between an inert indicator electrode in contact with the body fluid and a stable reference electrode connected to the body fluid by a salt bridge. The inert indicator electrode acts as a platform for electron transfer to or from the reference half cell. The indicator electrode may comprise platinum. The indicator electrode may comprise gold and graphite. The reference electrode may be stable hydrogen electrode (SHE), Ag/AgCl reference electrode or saturated calomel (SCE) reference electrode.

Any suitable assay method, or a combination of two or more such assay methods, capable of measuring the overall redox activity of the body fluid may be used with the methods of the present invention. The overall redox activity of the body fluid may be assayed by reacting the body fluid with at least one redox indicator. As used herein, the term "redox indicator" refers to a molecule that undergoes a significant measurable change upon being reduced or oxidized by exchanging electron, proton or hydrogen atom with any biochemical component of the body fluid under examination.

A redox indicator may be a reducing agent, oxidizing agent or radical. The measurable change may be changes in color, fluorescence, chemiluminescence, electromagnetic radiation or any other suitable changes that may be assayed. The amount of the redox indicator reduced or oxidized may be directly correlated with the overall redox activity of the body fluid, which in turn is correlated with fetal gender, or the type of the ovum being produced. The redox indicator may be a chromogenic chemical capable of changing color upon being reduced or oxidized. The amount of the chromogenic chemical being reduced or oxidized can be measured by the difference in absorbance of the body fluid at a specific wavelength before and after the reduction/oxidation reaction.

Below are presented various types of redox assays that may be used to determine the overall redox activity of the body fluid such as urine. The overall redox activity of the body fluid may be determined by comparison with at least one standard where the sex of the fetus is known, or where the gender specific compatibility of the ovum is known. The comparative levels of the redox activity of the urine samples are shown in Table 1. The particular condition in each assay may be determined by a person of ordinary skill in the art without undue experimentation.

The overall reducing activity of a body fluid may be assayed using a heteropoly acid or its corresponding salts. Heteropoly acids are a class of acids each comprising a particular combination of metal, hydrogen, oxygen and other non-metal atoms. Specifically, a heteropoly acid contains a metal termed addenda atom, such as tungsten, molybdenum or vanadium; oxygen; a element termed hetero atom generally from the p-block of the periodic table, such as silicon, phosphorus or arsenic; and acidic hydrogen atoms. Two of the better known heteropoly acids are phosphotungstic acid (PTA) with the formula $H_3PW_{12}O_{40}$ and phosphomolybdic acid with the formula $H_3PMo_{12}O_{40}$.

The phosphotungstic and phosphomolybdic acids are very sensitive to reduction, and yield highly colored compounds even upon moderate reduction. Wu. Contributions to the chemistry of phosphomolybdic acid, phosphotungstic acid and allied substances. *J. Biol. Chem.* 1920. XLIII, 1: 189-220. Under acidic condition, PTA associates with proteins and forms precipitates in solution. Phosphotungstate: a "universal" (nonspecific) precipitant for polar polymers in acid solution. *Journal of Histochemistry and Cytochemistry*. J. E. Scott. 1971. 19, 11, 689. Besides proteins, PTA also has an affinity for carbohydrates at low pH. Pease D C. *J. Ultrastructure Res.* 1966. 15: 555. As pH of its solution increases, a heteropoly acid generally decomposes to its simpler constituent acids, but can be regenerated by re-acidification.

The assay using PTA may be conducted under mild conditions. With a PTA assay, the urine from a female carrying a female fetus will have a comparatively higher overall reducing activity as compared with urine from a female carrying a male fetus. When a urine sample from a pregnant female carrying a male fetus contacts PTA, PTA remains intact in the urine and forms insoluble complexes with urinary proteins and glycoproteins. Thus, this urine sample appears as a white colloidal suspension in the PTA assay for at least about 12 hours.

In contrast, for urine from a pregnant female carrying a female fetus, although PTA initially forms insoluble complexes with urinary proteins and glycoproteins, the complexes gradually decrease as PTA is being reduced by the urine. The reaction mixture becomes transparent over time. The time period for the reaction mixture to turn from a white colloidal suspension to clear solution may vary among different urine samples. In some embodiments, the time period may range from about 5 minutes to about 12 hours. Shorter or longer time periods may also be appropriate, such as about 1 minute, 2 minutes, 3 minutes, 4 minutes, 13 hours, 14 hours, 15 hours, 16 hours, 17 hours, 18 hours, 19 hours and 20 hours.

Tungsten or molybdenum is preferred as the addenda atom of the heteropoly acid or its salts used in the present invention. A heteropoly acid or its salts may consist of one or more than one type of addenda atoms. The combinations of the addenda atoms include molybdenum and tungsten, vanadium and molybdenum, and vanadium, molybdenum and tungsten. The hetero atom of a heteropoly acid or its salts is selected from the group consisting of phosphorus, arsenic, silicon and germanium. Phosphorus is preferred as the hetero atom. Heteropoly acids or their salts comprising molybdenum and phosphorus, molybdenum and arsenic, or tungsten and phosphorus are preferred embodiments. A heteropoly acid or its salts may be selected from the group consisting of phospho-12-molybdic acid, phospho-18-molybdic acid, 12-molybdoarsenic acid, 18-molybdoarsenic acid, 11-molybdo-1-vanadophosphoric acid, 10-molybdo-2-vanadophosphoric acid, phospho-12-tungstic acid, phospho-18-tungstic acid, phospho-24-tungstic acid and 9-molybdo-3-vanadophosphoric acid. Phospho-18-molybdic acid, phospho-12-tungstic acid, phospho-18-tungstic acid and phospho-24-tungstic acid are preferred embodiments. Heteropoly acids and their salts may be used individually or their combinations may be used.

An excellent correlation ($R^2 > 0.99$) was reported between total phenolic contents as measured by Folin-Ciocalteau reagent (Phosphomolybdic-Phosphotungstic Acid Reagents) and antioxidant activity as measured by FRAP, TEAC or DPPH (1,1-Diphenyl-2-Picrylhydrazyl) assays. Connor et. al. Changes in fruit antioxidant activity among blueberry cultivars during cold temperature storage. *J. Aaric. Food Chem.* 2002, (50), 893-989. Because these assays are based on similar redox reactions, it is important to use one assay that is commonly accepted and validated. The total phenols assay by Folin-Ciocalteau reagent is conducted at basic conditions (e.g., pH 10). The PTA test may also be performed at a basic pH. Since each of the three main estrogens (i.e., estradiol, estriol, estrone) has a phenol group which contributes to their antioxidant properties, reduction of heteropoly acids has been seen as a measure of both the phenolic contents and antioxidant properties. Therefore, under these conditions, the phosphotungstic reducing capacity correlates with radical scavenging capacity of estrogens in processed urine sample.

The overall redox activity of a body fluid may be assayed by a chromogenic chemical comprising an oxidation-reduction sensitive metallic ion. The metallic ion may be selected from the group consisting of copper, iron, chromium, tungsten, molybdenum ions in an oxidized state.

The chromogenic chemical may be a metal-organic complex which, due to its extremely high oxidizing activity (correlated with high redox potential), can be reduced by many reducing agents and undergo change in color. The ferric reducing/antioxidant power (FRAP) assay can be used to assay the overall reducing activity of a body fluid. The ferric tripyridyltriazine (Fe(III)-TPTZ) complex is reduced under acidic conditions by a reducing agent to form ferrous tripyridyltriazine (Fe(II)-TPTZ). Fe(III)-TPTZ is yellow in color. The production of Fe(II)-TPTZ is easily detectable and measurable because of its intense blue color with a maximum absorption at wavelength 593 nm.

The FRAP assay may be conducted under harsh conditions, where the urine from a female carrying a male fetus will have a comparatively higher overall reducing activity than urine from a female carrying a female fetus. Accordingly, a urine sample from a female carrying a male fetus is able to reduce Fe(III) to Fe(II), or Fe(III)-TPTZ to Fe(II)-TPTZ, with the reaction mixture turning dark blue. In contrast, a urine sample from a female carrying a female fetus is not able to reduce Fe(III), or Fe(III)-TPTZ, and thus, the reaction mixture remains yellow.

Potassium ferricyanide may also be used in the FRAP assay. Oyaizu. Studies on products of Browning reaction. *J. Nutrition.* 44: 307-315 (1986). Under the harsh conditions of the FRAP assay, the urine from a female carrying a male fetus will have comparatively higher overall reducing activity than urine from a female carrying a female fetus. Accordingly, a urine sample from a female carrying a male fetus is able to reduce potassium ferricyanide to potassium ferrocyanide, which is then able to form dark blue product when ferric chloride is added. In contrast, a urine sample from a female carrying a female fetus is not able to reduce potassium ferricyanide, and, thus, the reaction mixture remains golden yellow or faint green in color.

For fraternal multiples with different genders, when the FRAP assay is conducted, the urine with a comparatively higher overall reducing activity than urine from a female carrying a female fetus correlates with at least one male fetus, whereas the urine with comparable overall reducing activity to urine from a female carrying a female fetus correlates with at least two female fetuses.

The overall reducing activity of a body fluid may be assayed by the reduction of $Cu^{2+}$ to $Cu^+$, which may be detected by the complex formation between $Cu^+$ and bathocuproine. The amount of $Cu^+$ being generated correlates with the overall reducing activity of the body fluid. The $Cu^+$-bathocuproine complex is stable and has a maximum absorption at wavelength around 480-490 nm. In one embodiment, the amount of $Cu^+$ being generated is quantified by referring to a standard curve, which uses uric acid as the reducing agent.

The overall reducing or antioxidant activity of the body fluid may be assayed by its ability to capture a free radical in the presence of a redox indicator. In one embodiment, the radical is hydroxy radical (OH.) generated either by a hydroxyl radical-generating system or internally within the body fluid, with sodium salicylate as the redox indicator. In the absence of other antioxidant (or reducing agent), the colorless salicylate ion reacts with OH. to produce dihydroxybenzoic acid, which is blue in color and has a maximum absorption at wavelength 510 nm. When other antioxidant (or reducing agent) is present, hydroxyl radical is sequestered or trapped by this antioxidant (or reducing agent) instead. As a result, sodium salicylate stays intact and the reaction mixture remains colorless.

In another embodiment, the overall redox activity of the body fluid may be assayed by its ability to facilitate the generation of free radicals. The assay reagents may comprise sodium salicylate and a hydroxyl radical generating system including a ferric compound, such as ferric sulfate, and $H_2O_2$. When the reducing agent is present, it reduces ferric to ferrous, which results in further reduction of $H_2O_2$ to generate hydroxyl radical OH. through the Fenton reaction. Salicylate ion then reacts with OH. to produce dihydroxybenzoic acid that is blue in color. The reaction is diagramed below.

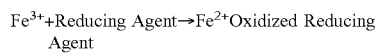

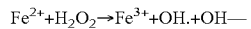

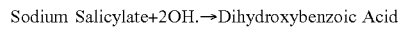

In the absence of the reducing agent, no OH. is generated. As a consequence, sodium salicylate remains colorless.

There are various ways to generate radicals. For example, in addition to Fenton reactions, hydroxyl radicals can be generated by a) ultrasound (Free radical generation by ultrasound in aqueous and nonaqueous solutions. P. Riesz et al. *Env. Health Perspectives* 1985 (64) 233-252); b) xanthine/xanthine oxidase system (Generation of hydroxyl radical by enzymes, chemicals, and human phagocytes in vitro. John E. Repine et. al. *J. Clin. Invest.* 1979 (64) 1642-1651); c) electron paramagnetic resonance (Hydroxyl radical generation by electron paramagnetic resonance as a new method to monitor ambient particulate matter composition. Tingming Shi et. al. *J. Environ.* 2003, (5), 550-556); d) phagocytic activity of human leukocytes (human granulocyte generation of hydroxyl radical. Stephen J. Weiss et. al. J. Exp. Med. 1978 (147) 316-323); e) oxidation of certain chemicals (Enhanced generation of hydroxyl radical and sulfur trioxide anion radical from oxidation of sodium sulfite, nickel (II) sulfite, and nickel subsulfide in the presence of nickel (II) complexes. Xianglin Shi et. al. *Environ. Health Perspectives* 1994, 102(3)); f) photolysis of N-hydroxypyridinethiones (Photolysis of N-hydroxypyridinethiones: a new source of hydroxyl radicals. Bernd Epe et. al. *Nucleic Acids Res.* 1996, 24(9), 1625-1631); g) UV-induced photolysis of hydrogen peroxide and UV irradiation of particles of titanium dioxide, etc.

Additionally, hydroxyl radicals can be produced internally through contribution of iron from hemoglobin and its metabolites in urine in the presence of $H_2O_2$. Accordingly, hemoglobin has been regarded as an internal Fenton reagent. In the presence of a superoxide anion-generating system (e.g., hypoxanthine and xanthine oxidase), haemoglobin promotes hydroxyl radical formation in a dose dependent fashion. Hydroxyl radical may be generated primarily via reaction between the ferrous heme iron and $H_2O_2$. (Hemoglobin: A biologic Fenton Reagent. Sayed M. H. Sadrzadeh et. al. *J. Biol. Chem.* 1984, 259(23), 14354-14356). The $H_2O_2$ decomposes heme and its metabolites, and releases iron from the protein (Formation of hydroxyl radicals from hydrogen peroxide in the presence of iron. Is haemoglobin a biological Fenton reagent? Alain Puppo et. al., *Biochem J.* 1988 (249), 185-190.)

The applicant has observed that urine samples from women with female gender related characteristics (e.g., a pregnant woman carrying a female fetus) have higher porphyrin content than that of women with male gender related characteristics (e.g., a pregnant woman carrying a male fetus). This may be due to relatively higher degradation of heme molecules occurring in-vivo in women with female gender related characteristics.

The present invention provides a method of determining the gender of an unborn child comprising the steps of: (a) contacting a body fluid from a pregnant female with free radicals; (b) measuring free radical scavenging activity of the body fluid; (c) comparing the free radical scavenging activity of the body fluid with at least one standard; and (d) determining the gender of the unborn child.

The free radical scavenging activity may be measured by methylene blue. Methylene blue may be in a solid form, in a solution, or attached to a solid surface. In one embodiment, the gender of an unborn child is determined to be female if there is substantially no decolorization of methylene blue; the gender of an unborn child is determined to be male if there is decolorization of methylene blue within about 1 hour.

The free radicals may be DPPH (1,1-Diphenyl-2-Picrylhydrazyl) radicals, or galvinoxyl radical, i.e., GV (2,6-di-tert-butyl-α-(3,5-di-tert-butyl-oxo-2,5-cyclohexanedien-1-ylidene)-p-tolyloxy) radical. DPPH may be in a solid form, in a solution, or attached to a solid surface. The free radicals may be hydroxyl radicals or superoxide radicals. The hydroxyl radicals may be generated internally or externally using heat, ultrasound, irradiation, photolysis, electron paramagnetic resonance, electrolysis, chemical, electrochemical or enzymatic means. The hydroxyl radicals may be generated by the Fenton reaction (see above for the reaction scheme). The Fenton reaction may use iron ions, copper ions or titanium dioxide as catalysts.

In one specific example, when one drop (or two to three drops) of a processed urine sample from a non-pregnant or pregnant female is added to 1 ml (or 0.5 ml) of 100 ppm solution of DPPH radical in methanol (or in acetonitrile), the rate of decolorization of the DPPH solution is faster in samples having female gender related characteristics (e.g., a urine sample from a pregnant woman carrying a female fetus) compared to samples having male gender related characteristics (e.g., a urine sample from a pregnant woman carrying a male fetus). Specifically, when the rate of disappearance of DPPH's purple color is measured using a spectrophotometer at 517 nm, the area under curve (AUC) for a sample having female gender related characteristics is significantly lower than that of a sample having male gender related characteristics. The difference may be observed with the naked eye. Whereas a sample having female gender related characteristics may completely decolorize within 2 minutes, a sample having male gender related characteristics may take much longer time (e.g., from about 1 hour to about 12 hours) or even never completely decolorize in several days. The length of time for DPPH to decolorize may vary depending on factors such as the properties of the DPPH reagent used, the concentration of the DPPH solution used, the estrogens in the sample, etc.

Estrogens may be the only radical scavenging components in an aged urine sample. Therefore, a urine sample having female gender related characteristics will have higher radical scavenging activity as compared to a urine sample having male gender related characteristics. Inclusion of additional radicals, like DPPH, induces competition between hydroxyl radicals and DPPH radicals. By modifying urine processing protocol, it is possible to suppress or promote the generation of hydroxyl radicals. When hydroxyl radical generation is diminished or blocked, estrogens scavenge DPPH radicals instead and a sample having female gender related characteristics will decolorize relatively much faster than a sample having male gender related characteristics. A sample having female gender related characteristics may decolorize in less than about 1 minute, or less than about 5 seconds, whereas a sample having male gender related characteristics may decolorize after about 1 hour, after about 2 hours, after about 3 hours or even longer.

On the other hand, when the sample processing conditions are such that hydroxyl radical production is promoted or retained, there is competition between DPPH radicals and hydroxyl radicals to react with estrogens. The unused DPPH radicals appear to preferably be reduced by an unused portion of hydroxyl radicals. Under such conditions, decolorization of DPPH is faster in a sample having male gender related characteristics than that of a sample having female gender related characteristics. A sample having male gender related characteristics may decolorize in about 15 minutes, whereas a sample having female gender related characteristics may take longer to decolorize, for example, about 1 hour to about 24 hours, about 1 hour to about 12 hours, about 1 hour, about 12 hours, or about 24 hours. Ultimately both types of samples will decolorize from purple to yellow. Due to variability of sex hormone levels in samples, it is relatively difficult to clearly evaluate the gender related characteristics under these conditions, and, as a result, the error rate may be high.

Therefore, when DPPH radical is being used, a preferable embodiment would be to block the hydroxyl radical generation to get an accurate evaluation of fetal gender related characteristics.

The overall redox activity of the body fluid may also be detected using redox sensitive polymers such as polyaniline. Polyaniline is polymerized from the aniline monomer and has the following structure,

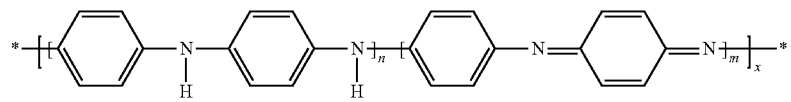

where x is half the degree of polymerization. Polyaniline can be found in one of three oxidation states. The leucoemeraldine form of polyaniline (n=1, m=0) is the fully reduced state and is white or colorless. Pernigraniline (n=0, m=1) is the fully oxidized state and is blue or violet. The emeraldine (n=m=0.5) form of polyaniline is the intermediate state and is green or blue. The color change associated with polyaniline in different oxidation states may be exploited to use polyaniline as a redox indicator. Huanga et al. Development and characterization of flexible electrochromic devices based on polyaniline and poly(3,4-ethylenedioxythiophene)-poly(styrene sulfonic acid). *Electrochimica Acta.* 51, 26: 5858-5863 (2006).

In another embodiment, the overall reducing activity of a body fluid may be assayed by an in situ methodology. For example, a redox indicator, which may be selected from the group consisting of thionine, toluidine blue O and cresyl violet, is immobilized to agarose beads. The agarose beads are then packed into a flow cell. The body fluid is allowed to pass through the flow cell and the redox states of the redox indicator is monitored by spectrophotometry. Jones. Evaluation of immobilized redox indicators as reversible, in situ redox sensors for determining Fe(III)-reducing conditions in environmental samples. *Talanta.* 2001. 55, 4: 699-714.

Voltammetry may be used in the present invention. Many studies have used voltammetry to assay antioxidant activities. (Chavion S. et al. The use of cyclic voltammetry for the evaluation of the antioxidant capacity. *Free Radic. Biol. Med.* 2000, 28, 860-870). Voltammetric assays are based on cyclic voltammetry (CV), square wave voltammetry (SWV), and differential pulse voltammetry (DPV). Antioxidants are oxidized under a typical voltage which results in a faradaic current proportional to the concentration of antioxidants (Supalkova V. et al. Electroanalysis of plant thiols. *Sensors.* 2007, 7, 932-959). In assaying antioxidants in biological matrices, a close correlation was found for the SWV results and the FRAP data. One of the advantages of SWV is the ability to distinguish two basic types of low molecular weight antioxidants, i.e., ascorbic/uric acids and thiol-containing molecules. SWV can be conducted within a relatively short period of time with or without prior sample modification. (Miroslav P. et al., Ferric reducing antioxidant power and square wave voltammetry for assay of low molecular weight antioxidants in blood plasma. *Sensors* 2009, (9), 9094-9103).

The overall redox activity of a body fluid may be detected by general reducing sugar tests using copper ion, neocuproine or alkaline ferricyanide method with or without color formation with o-phenanthroline complex. Prado et al. *Phytochem. Analysis.* 9 (2): 58-62 (1998).

The overall redox activity of the body fluid may also be detected by the Oxygen Radical Absorbance Capacity (ORAC) assay, which measures both lipophilic and hydrophilic antioxidant capacity using the same peroxyl radical generator. The ORAC assay measures the oxidative degradation of a fluorescent molecule (such as beta-phycoerythrin or fluorescin) after being mixed with free radical generators such as azo-initiator compounds. Azo-initiator compounds produce peroxyl free radical, which damages the fluorescent molecule resulting in loss of fluorescence. Antioxidant or reducing agent such as estrogen is able to protect the fluorescent molecule from the oxidative degeneration. The degree of protection by the antioxidant or reducing agent may be quantified using a fluorometer. Williams et al. A comparison of mammalian and plant estrogens on vascular reactivity in young and old mice with or without disruption of estrogen receptors. *Current Topics in Nutraceutical Res.* 2, 4: 191 (2004).

The present invention provides a method of determining the gender of an unborn child comprising the steps of: (a) performing oxygen radical absorbance capacity (ORAC) assay on a body fluid from a pregnant female; (b) calculating the ORAC value; and, (c) comparing the ORAC value from step (b) with at least one standard to determine the gender of the unborn child.

The present invention further provides a method of determining the gender of an unborn child comprising the steps of: (a) performing hydroxyl radical antioxidant capacity (HORAC) assay on a body fluid from a pregnant female; (b) calculating the HORAC value; (c) comparing the HORAC value from step (b) with at least one standard; and (d) determining the gender of the unborn child.

The HORAC assay is based on the oxidation of fluorescein by hydroxyl radicals via a classic hydrogen atom transfer (HAT) mechanism. Free radicals are generated by hydrogen peroxide ($H_2O_2$). The hydroxyl radicals thus generated quench the fluorescence of fluorescein over time. The antioxidants block the hydroxyl radical mediated oxidation of fluorescein until all of the antioxidant activity in the sample is exhausted, after which the $H_2O_2$ radicals react with and quench the fluorescence of fluorescein. The area under the fluorescence decay curve (AUC) is used to quantify the total hydroxyl radical antioxidant activity in a sample and is compared to a standard curve obtained using various concentrations of gallic acid. The fluorescent HORAC assay provides a direct measurement of antioxidant capacity against hydrophilic chain-breaking hydroxyl radicals.

When fluorescein is used as radical quenching chemical, the gender of the unborn child is determined to be male if the HORAC value from step (b) is less than about 5000; the gender of the unborn child is determined to be female if the value from step (b) is greater than about 6000. When other compounds (such as methylene blue) are used as radical quenching chemicals, the HORAC value from step (b) may have different range for male and/or female unborn child.

In one embodiment, there is provided a method of determining the gender of an unborn child comprising the steps of: (a) performing hydroxyl radical antioxidant capacity (HORAC) assay on a body fluid from a pregnant female; (b) calculating the HORAC value; and (c) determining the gender of the unborn child to be male if the HORAC value from step (b) is less than about 5000, or to be female if the value from step (b) is greater than about 6000.

The reaction of a body fluid sample with methylene blue is similar to the HORAC test where a sample associated with female gender related characteristics (e.g., a urine sample from a pregnant woman carrying a female fetus) exhibits greater radical scavenging capacity. In a specific example, a hydroxyl radical generation system is provided with methylene blue being coated on a solid support (e.g., a piece of paper) and used as a hydroxyl radical probe. A urine sample from a female exhibiting male gender related characteristics (e.g., a pregnant woman carrying a male fetus) would decolorize methylene blue, forming a blue ring with a white center, whereas methylene blue mixed with a urine sample from a female exhibiting female gender related characteristics (e.g., a pregnant woman carrying a female fetus) would remain blue (e.g., no decolorization). Without being limited to any specific physiological mechanism, it is believed that in samples with female gender related characteristics, the hydroxyl radicals preferentially react with relatively higher amount of estrogens in the urine sample and do not decolorize methylene blue. In contrast, in samples exhibiting male gender related characteristics, there are less estrogens to absorb hydroxyl radicals, therefore leaving enough hydroxyl radicals to decolorize methylene blue. The rate of decolorization depends upon the type of urine sample as well as on the processing method.

Any suitable assays similar to the HORAC or ORAC assays can be used in the present invention. For these assays, any suitable free radical generators, and/or any suitable fluorescent molecules can be used.

The overall redox activity of the body fluid may be detected by the Antioxidant Capacity (AOC) assay using the 3-ethylbenzothiazoline-6-sulfonate (ABTS) system or TPTZ. Bahramikia et al. A comparison of Antioxidant Capacities of ethanol extracts of S. Hortensis and A. *Dracunculus* leaves. *Pharmacology Online* 2: 694-704 (2008).

The overall redox activity of the body fluid may be detected by the use of immobilized chromogenic radicals. In one embodiment, either of two stable lipophylic chromogenic radicals, DPPH (2,2-diphenyl-1-picrylhydrazyl) radical and GV (2,6-di-tert-butyl-α-(3,5-di-tert-butyl-oxo-2, 5-cyclohexanedien-1-ylidene)-p-tolyloxy) radical, is immobilized in plasticized polymer films, such as polyvinyl chloride (PVC) films. When the polymer film containing immobilized 2,2-diphenyl-1-picrylhydrazyl (DPPH) radical is reduced by a body fluid, it changes color irreversibly from purple (maximum absorption at wavelength 520 nm) to yellow. Steinberg et al. Chromogenic radical based optical sensor membrane for screening of antioxidant activity. *Talanta* 8: 15 (2006).

The overall redox activity of the body fluid may be detected by immunoassay such as immunofluorescence, using antibodies against gender related molecules; chemiluminescence; bioluminescence such as green fluorescent proteins; antibody-tagged gold nanoparticles of differing sizes; chemical tagging or fluorescent dyes. Kohen et al. Recent advances in chemiluminescence-based immunoassays for steroid hormones. *J. Steroid Biochem.* 27, 1-3: 71-79 (1987).

The overall oxidizing activity of the body fluid may be assayed by adding a source of ferrous ions to the body fluid, whereby oxidants in the sample oxidize at least a portion of the ferrous ions to ferric ions. Then a chromogenic compound is added to the sample, which reacts with at least a portion of the ferric ions. U.S. Patent Publication No. 20040259186.

The overall reducing activity of the body fluid may be assayed using reagents selected from the group consisting of ferricyanide salts, dichromate salts, permanganate salts, vanadium oxides, dichlorophenolindophenol, osmium bipyridine complexes, and quinones. The overall oxidizing activity of the body fluid may be assayed using reagent selected from the group consisting of iodine, triiodide salts, ferrocyanide salts, ferrocene, $[Cu(NH3)_4]^{2+}$ salts and $[Co(NH3)_6]^{3+}$ G salts. The redox indicator of the present methods may be selected from the group consisting of 2,6-dichlorophenolindophenol (DCPIP), 3,3',5,5'tetramethylebenzidine (TMB), 1,4-phenylenediamine (DMPDA), Phenanthridine, 2,6-Dichloroindophenol, 2,2'-Azino-bis(3-ethylbenzthiazoline-6-sulfonic) acid, N,N-Dimethylphenylenediamine, 2-Amino-p-cresol (APC), Xylenol orange, 8-Hydroxy-7-iodo-5-quinoline-sulfonic acid and 4,5-Dihydroxy-1,3-benzene-di-sulfonic acid.

The present invention provides a method of determining the gender of an unborn child comprising the steps of: (a) performing the HORAC assay on a body fluid from a pregnant female; (b) measuring levels of testosterone (T) and estrogens (E) in the body fluid, wherein step (b) can be performed before or after step (a); (c) calculating the value of HORAC/(E/T), wherein E/T is the ratio of the level of testosterone to the level of estrogens, and wherein the value of HORAC/(E/T) is the ratio of the HORAC value to the E/T ratio; and, (d) determining the gender of the unborn child to be male if the value of HORAC/(ET) from step (c) is less than about 150, or to be female if the value from step (c) is greater than about 200.

Also provided in the present invention is a method of determining the gender of an unborn child comprising the steps of: (a) performing the HORAC assay on a body fluid from a pregnant female; (b) measuring levels of testosterone (T), estrogens (E), progesterone (P) and gonadotropins (G) in the body fluid, wherein step (b) can be performed before or after step (a); (c) calculating the value of HORAC/[E−(T+P+G)], wherein [E−(T+P+G)] is the difference between the level of estrogens (E) and the total levels of testosterone (T), progesterone (P) and gonadotropins (G), and wherein the value of HORAC/[E−(T+P+G)] is the ratio of the HORAC value to the [E−(T+P+G)] value; (d) comparing the HORAC/[E−(T+P+G)] value from step (c) with at least one standard; and (e) determining the gender of the unborn child.

The present invention further provides a method of determining the gender of an unborn child comprising the steps of: (a) performing the HORAC assay on a body fluid from a pregnant female; (b) measuring levels of testosterone (T), estrogens (E), progesterone (P) and gonadotropins (G) in the body fluid, wherein step (b) can be performed before or after step (a); (c) calculating the value of HORAC/[(E+T)/(P+G)] wherein [(E+T)/(P+G)] is the ratio of the total levels of estrogens (E) and testosterone (T) to the total levels of progesterone (P) and gonadotropins (G), and wherein the value of HORAC/[(E+T)/(P+G)] is the ratio of the HORAC value to the [(E+T)/(P+G)] value; (d) comparing the HORAC/[(E+T)/(P+G)] value from step (c) with at least one standard; and (e) determining the gender of the unborn child.

The present invention provides a method of determining the gender of an unborn child comprising the steps of: (a) contacting a body fluid from a pregnant female with a solid surface having antibodies specific to estrogens, antibodies specific to testosterone, antibodies specific to progesterone and antibodies specific to hCG-beta; (b) contacting the solid surface from step (a) with at least one redox indicator; (c) measuring redox activity of the solid surface; (d) comparing the redox activity of the solid surface with at least one standard; and (e) determining the gender of the unborn child. Sex hormones may alternatively be released from the solid surface before the redox activity of the sex hormones is measured.

The redox activity may be measured by Ferric reducing/antioxidant power (FRAP) assay, and/or Ferric reducing/antioxidant power assay using ferric tripyridyltriazine (FRAP-TPTZ).

The present invention also provides methods for pre-conception baby gender planning by assaying the overall redox activity and or radical scavenging activity of a female's urine or other body fluid. The body fluid may be obtained anytime during a menstrual cycle, but preferably around the time of ovulation.

Without being limited to any specific physiological mechanism, it is believed that ovulation generates at least two types of uterine environments during alternate menstrual cycles, presumably due to the release of two different types of ova. One type of ovum is associated with uterine environment to be compatible with fertilization by a Y chromosome-bearing sperm to produce a male fetus, whereas the other type of ovum is associated with uterine environment to be compatible with fertilization by an X chromosome-bearing sperm to produce a female fetus. The overall redox activity of the maternal urine correlates with the gender specific compatibility of the ovum released in a particular menstrual cycle.

Under harsh assay conditions or with aging, the urine sample of a non-pregnant female carrying an ovum compatible with fertilization by a Y chromosome-bearing sperm will have comparatively higher reducing activity than urine from a non-pregnant female carrying an ovum compatible with fertilization by an X chromosome-bearing sperm (see Table 1 for summary) It is believed that a female produces two types of ova which generally alternate every month, i.e., if in one month the ovum being produced is compatible with fertilization by an X chromosome-bearing sperm, then in the next month the ovum being produced is compatible with fertilization by a Y chromosome-bearing sperm. The pre-conception urine assay can help a couple conceive a baby having a desired gender. For example, if a couple desires a baby girl, it is recommended that they plan to conceive in any month when the ovum being produced is compatible with fertilization by an X chromosome-bearing sperm. Similarly, if a couple wishes a baby boy, it is recommended that they plan to conceive in any month when the ovum being produced is compatible with fertilization by a Y chromosome-bearing sperm. The purpose of the present pre-conception methods is to increase the chances of conceiving a baby of the desired gender by advising appropriate menstrual cycles for conception.

The present invention provides a method for pre-conception baby gender planning comprising the steps of: (a) contacting a body fluid from a non-pregnant female with at least one redox indicator; (b) measuring redox activity of the body fluid; and, (c) comparing the redox activity of the body fluid with at least one standard to determine gender-specific compatibility of the ovum released in a menstrual cycle. The body fluid may be obtained near ovulation or middle of the menstrual cycle. The body fluid may be processed prior to step (a).

If two urine samples collected in two consecutive months manifest different redox activities, it suggests that the female has a regular alternating ovulation pattern as described above. If both urine samples demonstrate comparatively higher reducing activity than urine from a non-pregnant female carrying an ovum compatible with fertilization by an X chromosome-bearing sperm, the female may have an irregular ovulation pattern which is difficult to normalize according to the present invention. If both urine samples demonstrate comparatively higher oxidizing activity than urine from a non-pregnant female carrying an ovum compatible with fertilization by a Y chromosome-bearing sperm, the female's irregular ovulation pattern may be normalized through diet and exercise.

As described above, any suitable assay method, or a combination of two or more such assay methods, capable of measuring the overall redox activity of the body fluid may be used with the present pre-conception assay or the present post-conception assay.

The overall redox activity of the body fluid during a menstrual cycle within which a female conceives is continued and maintained throughout pregnancy. Namely, if her pre-conception body fluid has a comparatively higher overall reducing activity than that of the body fluid from a non-pregnant female carrying an ovum compatible with fertilization by an X chromosome-bearing sperm under the harsh condition (for example, in the FRAP assay), her ovum is compatible with fertilization by a Y chromosome-bearing sperm. Consistently, her post-conception urine sample would also have a higher overall reducing activity than that of urine from a female carrying a female fetus, which is correlated with a male fetus. Conversely, if her pre-conception urine sample has a higher overall oxidizing activity than that of urine from a non-pregnant female carrying an ovum compatible with fertilization by a Y chromosome-bearing sperm under harsh conditions, her ovum is compatible with fertilization by an X chromosome-bearing sperm. Likewise, her post-conception urine sample would also have a higher overall oxidizing activity than that of urine from a female carrying a male fetus, which is correlated with a female fetus.

Provided in the present invention is a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating [E−(T+P+G)] as the difference between the level of estrogens (E) and the total levels of testosterone (T), progesterone (P) and gonadotropins (G); (c) comparing the [E−(T+P+G)] value from step (b) with at least one standard; and (d) determining the gender specific compatibility of the ovum released in the menstrual cycle.

In one embodiment, there is provided a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating [E−(T+P+G)] as the difference between the level of estrogens (E) and the total levels of testosterone (T), progesterone (P) and gonadotropins (G); and (c) determining the gender specific compatibility of the ovum released in the menstrual cycle to be male if the [E−(T+P+G)] value from step (b) ranges from about 300 to about 1,500, or to be female if the [E−(T+P+G)] value from step (b) ranges from about −10 to about −800.

The present invention provides a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating (E+T)/(P+G) as the ratio of the total levels of estrogens (E) and testosterone (T) to the total levels of progesterone (P) and gonadotropins (G); (c) comparing the ratio (E+T)/(P+G) from step (b) with at least one standard; and (d) determining the gender specific compatibility of the ovum released in the menstrual cycle.

In one embodiment, there is provided a method of determining gender specific compatibility of an ovum released in a menstrual cycle for pre-conception baby gender planning comprising the steps of: (a) measuring levels of testosterone (T), estrogens (E), progesterone (P) and gonadotropins (G) in a body fluid from a non-pregnant female; (b) calculating (E+T)/(P+G) as the ratio of the total levels of estrogens (E) and testosterone (T) to the total levels of progesterone (P) and gonadotropins (G); and (c) determining the gender specific compatibility of the ovum released in the menstrual cycle to be male if the (E+T)/(P+G) ratio from step (b) is greater than about 1.4, or to be female if the (E+T)/(P+G) ratio from step (b) is less than about 1.2.

The present invention also provides a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) calculating the HORAC value; (c) comparing the HORAC value from step (b) with at least one standard; and (d) determining the gender specific compatibility of the ovum released in the menstrual cycle.

In one embodiment, there is provided a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) calculating the HORAC value; and (c) determining the gender specific compatibility of the ovum released in the menstrual cycle to be male if the HORAC value from step (b) is less than about 5000, or to be female if the value from step (b) is greater than about 6000.

The present invention further provides a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T) and estrogens (E) in the body fluid, wherein step (b) can be performed before or after step (a); (c) calculating the value of HORAC/(E/T), wherein E/T is the ratio of the level of testosterone to the level of estrogens, and wherein the value of HORAC/(E/T) is the ratio of the HORAC value to the E/T ratio; (d) comparing the ratio HORAC/(E/T) from step (c) with at least one standard; and (e) determining the gender specific compatibility of the ovum released in the menstrual cycle.

In one embodiment, there is provided a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T) and estrogens (E) in the body fluid, wherein step (b) can be performed before or after step (a); (c) calculating the value of HORAC/(E/T), wherein E/T is the ratio of the level of testosterone to the level of estrogens, and wherein the value of HORAC/(E/T) is the ratio of the HORAC value to the Elf ratio; and (d) determining the gender specific compatibility of the ovum released in the menstrual cycle to be male if the value of HORAC/(ET) from step (c) is less than about 150, or to be female if the value from step (c) is greater than about 200.

The present invention provides a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T), estrogens (E), progesterone (P) and gonadotropins (G) in the body fluid, wherein step (b) can be performed before or after step (a); (c) calculating the value of HORAC/[E−(T+P+G)], wherein [E−(T+P+G)] is the difference between the level of estrogens (E) and the total levels of testosterone (T), progesterone (P) and gonadotropins (G), and wherein the value of HORAC/[E−(T+P+G)] is the ratio of the HORAC value to the [E−(T+P+G)] value; (d) comparing the HORAC/[E−(T+P+G)] value from step (c) with at least one standard; and (e) determining the gender specific compatibility of the ovum released in the menstrual cycle to be male if the HORAC/[E−(T+P+G)] value from step (c) falls within a range of the standard with a male gender specific compatibility, or to be female if the HORAC/[E−(T+P+G)] value from step (c) falls within a range of the standard with a female gender specific compatibility.

The present invention provides a method of determining gender specific compatibility of an ovum released in a menstrual cycle for pre-conception baby gender planning comprising the steps of: (a) performing hydroxyl radical antioxidant capacity (HORAC) assay on a body fluid from a non-pregnant female; (b) measuring levels of testosterone (T), estrogens (E), progesterone (P) and gonadotropins (G) in the body fluid, wherein step (b) can be performed before or after step (a); (c) calculating the value of HORAC/[(E+T)/(P+G)] wherein [(E+T)/(P+G)] is the ratio of the total levels of estrogens (E) and testosterone (T) to the total levels of progesterone (P) and gonadotropins (G), and wherein the value of HORAC/[(E+T)/(P+G)] is the ratio of the HORAC value to the [(E+T)/(P+G)] value; (d) comparing the HORAC/[(E+T)/(P+G)] value from step (c) with at least one standard; and (e) determining the gender specific compatibility of the ovum released in the menstrual cycle to be male if the HORAC/[(E+T)/(P+G)] value from step (c) falls within a range of the standard with a male gender specific compatibility, or to be female if the HORAC/[(E+T)/(P+G)] value from step (c) falls within a range of the standard with a female gender specific compatibility.

Also provided in the present invention method of determining gender specific compatibility of an ovum released in a menstrual cycle for pre-conception baby gender planning comprising the steps of: (a) contacting a body fluid from a non-pregnant female with free radicals; (b) measuring free radical scavenging activity of the body fluid; (c) comparing the free radical scavenging activity of the body fluid with at least one standard; and (d) determining gender specific compatibility of the ovum released in a menstrual cycle.

The free radicals may be DPPH (1,1-Diphenyl-2-Picrylhydrazyl) radical or GV (2,6-di-tert-butyl-α-(3,5-di-tert-butyl-oxo-2,5-cyclohexadien-1-ylidene)-p-tolyloxy radical.

When DPPH is used, in one embodiment, the gender specific compatibility of the ovum is determined to be female if decolorization of DPPH occurs within about 1 minute, whereas the gender specific compatibility of the ovum is determined to be male if decolorization of DPPH occurs after more than about 1 hour. In another embodiment, the gender specific compatibility of the ovum is determined to be male if decolorization of DPPH occurs within about 15 minutes, whereas the gender specific compatibility of the ovum is determined to be female if decolorization of DPPH occurs from about 1 hour to about 24 hours.

The free radical scavenging activity may be measured by methylene blue. In one embodiment, the gender specific compatibility of the ovum is determined to be female if there is substantially no decolorization of methylene blue, whereas the gender specific compatibility of the ovum is determined to be male if there is decolorization of methylene blue within about 1 hour.

The present invention further provides a method of determining gender specific compatibility of an ovum released in a menstrual cycle for pre-conception baby gender planning comprising the steps of: (a) contacting a body fluid from a non-pregnant female with a solid surface having antibodies specific to estrogens, antibodies specific to testosterone, antibodies specific to progesterone and antibodies specific to hCG-beta; (b) contacting the solid surface from step (a) with at least one redox indicator; (c) measuring redox activity of the solid surface; (d) comparing the redox activity of the solid surface with at least one standard; and (e) determining the gender specific compatibility of the ovum released in the menstrual cycle. The redox activity may be measured by Ferric reducing/antioxidant power (FRAP) assay or Ferric reducing/antioxidant power using ferric tripyridyltriazine (FRAP-TPTZ) assay.

The present invention further provides a method for determining the gender of a fetus that is within a female's uterus using remote detection devices. In vivo, a male fetus as a tissue mass has a higher overall oxidizing activity, or a lower reducing activity, than the surrounding maternal tissues, while a female fetus has a higher overall reducing or antioxidant activity than the surrounding maternal tissues. As is the case with post-conception or pre-conception urine tests, the redox activity of the fetal tissue or maternal tissue may be compared with a standard where the fetal gender is known. The remote detection device of the present invention may comprise of a probe. The device may detect the redox activity of different parts of a mother's internal tissues by non-invasively sensing the internal electrochemical signals, electromagnetic signals, or any other suitable physical and/or chemical signals. In one embodiment, internal redox potentials are detected by the remote detection device. In another embodiment, internal electronic charges are detected by the remote detection device. In a further embodiment, the remote detection device comprises an electroscope to detect electrochemical potential of fetal and maternal tissues.

The present remote detection device may comprise broadband diffuse optical spectroscopy. (Lee et al. Noninvasive in vivo monitoring of methemoglobin formation and reduction with broadband diffuse optical spectroscopy. *J. Appl. Physiology* 100: 615-622.) As known in the art, oxidation of proteins and amino acids generates ultra weak photon emission. The present remote detection device may comprise a sensitive photomultiplier system to detect the ultra weak photon emission that is associated with a male or female fetus. The present remote detection device may comprise electron paramagnetic resonance imaging (EPRI) by using redox sensitive paramagnetic contrast agents. (Yamada et el. Feasibility and assessment of non-invasive in vivo redox status using electron paramagnetic resonance imaging (EPRI). *Actd Radiol.* 43 (4):433-40 (2002).) The present remote detection device may comprise measuring the surface oxygen tension of organs. (Miller A. T. Jr. University of North Carolina at Chapel Hill. Tissue oxygen tension and the intracellular oxidation-reduction state. *Personal communication.*) Other suitable means may also be used for the present remote detection device. See, Wang. Remote electrochemical sensors for monitoring organic and inorganic pollutants. *Trends in Anal. Chem.* 16: 84 (1997). Balcom et al. Spatial and temporal visualization of two aqueous iron oxidation-reduction reactions by nuclear magnetic resonance imaging. *J. Chem Soc. Chem. Comm.* 1992: 312-313. Livesey et al. Measurement of tissue oxidation-reduction state with carbon-13 nuclear magnetic resonance spectroscopy. *Cancer Research.* 49: 1937-1940 (1989).

The change of the redox indicator may be analyzed with a scientific instrument, such as spectrophotometer, fluorometer, turbiditimeter, luminometer, fluorescence meter or colorimeter. The change in color of the chromogenic molecule may also be observed visually. The change of the redox indicator may be converted to digital signals which can be processed by digital, electronic or other sensing scientific instruments or materials. The scientific instrument may convert the assay results to a digital text response using any suitable means such as an electronic programming. In one embodiment, the instrument shows the text "It's a BOY" when the assay results suggest that the body fluid is from a female carrying a male fetus, and "It's a GIRL" when the assay results suggest that the body fluid is from a female carrying a female fetus. Similarly, for a pre-conception assay on the body fluid from a non-pregnant female, the instrument may show "Time for a baby boy" if the ovum produced in a particular menstrual cycle is compatible for fertilization by a Y chromosome-bearing sperm, and "Time for a baby girl" if the ovum produced in a particular menstrual cycle is compatible for fertilization by an X chromosome-bearing sperm.

The overall redox activity of the body fluid may be assayed using an electrochemical sensor, which is able to produce an electrochemically detectable signal upon being reduced or oxidized. In this case, a detection device may be used which comprises the redox indictor and has a disposable electrochemical cell, such as a thin layer electrochemical cell. The sensing electrode may consist of platinum, palladium, carbon, indium oxide, gold, iridium, copper, steel or mixture thereof. U.S. Pat. No. 6,638,415. WO2002/006806. Carbon nanotubes may be used for electrochemical sensing. Carbon nanotubes have the ability to promote electron transfer reactions when used as an electrode material in electrochemical reactions. U.S. Patent Publication No. 20060096870. Electrochemistry and electrogenerated chemiluminescence with a single faradaic electrode may be used for the present methods. It comprises of a faradaic working electrode and a capacitive counter electrode. When electrical energy is supplied in the presence of a body fluid, a faradaic charge transfer occurs wherein at least one of (i) light, (ii) current. (iii) voltage and (iv) charge can be measured to determine the presence or amount of analyte in a sample. WO2007/053191.

The steps of the methods of the present invention may be conducted by a human and/or a machine.

Encompassed by the present invention is a device configured to assay the body fluid, process the data (i.e., the assay results), and present the results (i.e., fetal gender related characteristics, for example, gender of the unborn child or biochemical environment of the uterus). The device may include pre-installed software (for user control, and output of information, as well as data processing/algorithmic data analysis etc.). The software may be designed based on the formulae described above. The device may contain at least one component to detect fluorescence, luminescence and/or other signal from within a chamber of the processing and/or sensing component.

In certain embodiments, blood may be added to a patch loaded with redox chemicals or radical scavenging chemicals as described herein to evaluate fetal gender related characteristics. For example, non-invasive transdermal membrane based diagnostic technology may be used according to the present invention. Additionally, special optics in electronic meter can detect the color change and provide the evaluation. (U.S. Pat. No. 6,503,198.)

The overall redox activity of the body fluid may be assayed using any suitable chemical, physical, biochemical or biological means. The overall redox activity of the body fluid may be assayed by contacting the body fluid with at least one microorganism such as a bacterium, and observing the physiological responses such as generation of colored product, movement of the bacterium's cilia. The overall redox activity of the body fluid may be assayed by redox-sensitive green fluorescent protein (GFP). Dooley et al. Imaging dynamic redox changes in mammalian cells with GFP indicators. *J. Biol. Chem.* 279, 24: 22284-22293 (2004). The overall redox activity of the body fluid may be measured by assaying fluorescence. In one embodiment, 5-cyano 2-3 ditolyl tetrazolium chloride (CTC) is used for the present assay. CTC's oxidized form, which is colorless and non-fluorescent, is readily reduced to fluorescent, insoluble CTC-formazan form.

The present methods may be modified to allow many samples to be tested and results read simultaneously using, for example, a microplate or multiplex microarray. Additionally, the present methods may be modified to allow multiple sex hormones in a sample to be tested and results read simultaneously using modern multiplex technology.

The present invention also provides an article of manufacture such as a kit comprising (a) a urine collecting vial; (b) a solid substrate comprising a redox indicator, radicals (or a radical-generating system) or radical-sensitive agents, wherein the redox indicator comprises at least one chromogenic chemical; (c) printed material instructing a woman to collect urine and contact the urine with the solid substrate; and (d) printed material instructing a woman to compare redox activity of the urine sample with at least one standard to determine the gender of the unborn child based on change in color in the chromogenic chemical. The kit may also comprise other chemicals for processing and/or assaying the overall redox activity of the body fluid. The printed matter may also indicate that, to determine the gender of an unborn child, the enclosed chemicals are to be used to assay the overall redox activity of the body fluid which will be compared with a standard. The printed material may instruct processing the urine prior to contact the urine with the solid substrate. The printed matter provides instructions as to how to use the enclosed chemicals for the test. Pictorial depictions of the instructions may be included in the printed matter. The printed matter may indicate that the body fluid is to be collected at any time during a pregnancy, starting from the first day of missed menstruation. The printed matter may also indicate that optimum results may be obtained if the body fluid is collected between the 5th and 15th week of pregnancy. The printed matter may include color standards for result interpretations and indicates the color (or a range of colors) that correlates with a male (or female) fetus. The chemicals may be provided in pre-measured quantities and may be in the form of solution, solid crystals or dry film. The chemicals may be placed in capped vials or bottles and placed in separate compartments. The chemicals may be absorbed or retained to solid supports and arranged sequentially to form a trickling column so as to ensure that various processes are conducted in a desired order. A kit may contain chemicals in sufficient amounts for one, two or more assays.

Similarly, the present invention further provides an article of manufacture such as a kit comprising necessary chemicals for processing and/or assaying the overall redox activity or the radical scavenging activity of the body fluid such as urine, as well as printed matter indicating that, to determine the suitable menstrual cycle for conceiving a baby of desired gender, the enclosed chemicals are to be used to assay the overall redox activity of the body fluid in at least two consecutive menstrual cycles. The printed matter may indicate that the body fluid may be collected at any time during a menstrual cycle. The printed matter may also indicate that optimum results may be obtained if the body fluid is collected around the ovulation period. The printed matter provides instructions as to how to use the enclosed chemicals for the test. The printed matter also includes color standards for result interpretations and indicates the color (or a range of colors) that correlates with an ovum compatible with fertilization by a Y chromosome-bearing sperm or an ovum compatible with fertilization by an X chromosome-bearing sperm. The printed matter indicates that two types of ova are produced in alternate months, and suggests that a woman who wishes to have a baby boy (or girl) try to conceive in alternate months, starting from the month an ovum compatible with fertilization by a Y chromosome-bearing (or X chromosome-bearing) sperm is ovulated.

The redox activity may be measured on a solid substrate which comprises a redox indicator, such as a chromogenic chemical, radicals (or a radical-generating system) or radical-sensitive agents. The chromogenic chemical may be impregnated on a strip. The article of manufacture of the present invention may be a test strip. The test strip may have a sample application site where the body fluid may be applied. The body fluid may then pass through various aging, processing, filtering, adsorbing or chromatographic media (e.g., to allow selective onward flow of desired sex hormones) which ultimately leads to the procedure of assaying the overall reducing or oxidizing activity and/or radical scavenging capacity of the sample by reacting with at least one redox indicator. The test strip may have more than one sample application site so that the body fluid may be applied at more than one site on the strip at the same time. The same body fluid applied at different sites on the strip may undergo different treatments and may meet different chromogenic chemicals or redox indicators. The overall reducing or oxidizing activity of the sample is then evaluated based on a specific pattern of colors or other measurable signals.

In one embodiment, a strip and a digital strip reader are provided according to the present invention which would assay and calculate the levels and/or the ratios of the sex hormones, and present the results in digital form.

Similarly, strips or kits containing various radical scavenging agents (such as methylene blue, DPPH or sodium salicylate) can be provided to evaluate radical scavenging capacity of a body fluid sample. Such strips or kits may or may not contain parts to process the body fluid (e.g., to remove interfering compounds in the body fluid before having appropriate hormones react with radical scavenging agents). A change in color or properties of the radical scavenging agents can then be used to evaluate fetal gender related characteristics.

An article of manufacture according to the present invention may contain one type of assay method, or two or more suitable assay methods.

In specific examples, the accuracy of a body fluid sample having female gender related characteristics can approach 100% if the processed sample shows all of the following: (a) a transparent PTA test after 12 hr; (b) a DPPH test with discolorization within about 2 minutes; (c) a blue FRAP test; and (d) a methylene blue test with no discolorization. Similarly, the accuracy of a body fluid sample having male gender related characteristics can approach 100% if the processed fluid shows all of the following a) a colloidal PTA test after 12 hr; b) a DPPH test with no discolorization; c) a golden yellow FRAP test; and (d) a methylene blue test with discolorization within about 12 hours. These observations can reverse depending upon sample processing technique and experimental conditions.

Essentially all of the methods, articles of manufacture described herein for determining the gender of an unborn child after conception may also be used to determine gender specific compatibility of the ovum released in a menstrual cycle or for evaluation of uterine environment before conception for, for example, pre-conception baby gender planning Different methods may be used on the same sample to for increased accuracy of results.

The methods of the present methods may be used to test a body fluid obtained from any mammal, such as a human, horse, cow, dog, monkey, sheep, pig and cat.

The present invention also provides a method of conceiving a baby of a desired gender in a female by applying to the female a pharmaceutical formulation with a specific sex hormone composition. Methods in the prior art are mostly based on modifying the pH value or ionic balance of the vaginal or uterine environment of a female, which have had limited clinical success. How to Choose the Gender of Your baby, a book by Ashley Spencer. Shettles et al., How to Choose the Sex of Your Baby. Broadway, 2006. The failure of those methods is largely due to the detrimental effects that the pH-modifying (or ionic balance-modifying) composition has on the sperm motility and viability. In contrast, the present methods are more natural. As described above, the uterine environment and the changes that it undergoes during the normal menstrual cycle can greatly influence gender selection. By taking advantage of these naturally occurring characteristics, methods have been developed in the present invention to amplify this natural selection process.

Specifically, as the hormonal composition of the uterus of a female (or a body fluid such as urine) prior to conception is associated with the compatibility of the uterus to a male or female conception, the present invention provides for methods of increasing the chance of conceiving a baby of a desired gender in a female by mimicking (or amplifying) a specific uterine environment. Therefore, by applying to the female a pharmaceutical formulation comprising sex hormones of certain composition, the uterine environment of the female can be modified to be compatible with conception of a baby of the desired gender. The pharmaceutical formulation may be applied, for example, near or around cervix uteri of the female. In certain embodiments, a pharmaceutical formulation with relatively higher overall reducing activity would create a uterine environment (or amplify an existing uterine environment) to increase the chances of conceiving a female baby. Similarly, a pharmaceutical formulation with relatively higher overall oxidizing activity would create a uterine environment (or amplify an existing uterine environment) to increase the chances of conceiving a male baby. It should be noted that in vivo conditions are similar to the mild assaying conditions of the present invention, and that estrogens behave as reducing agents whereas testosterone behaves as an oxidizing agent under in vivo conditions.

Table 2 tabulates an example of the pharmaceutical formulations that may be applied to a female to conceive either a boy or a girl. The pharmaceutical formulation may be in any suitable form, including, but not limited to, a gel, a solution, a cream, a lotion, an ointment, a foam or a paste. For each type of formulation, the concentration ranges of the sex hormones, as well as the optimum concentrations, are shown.

TABLE 2

| Hormone | Concentration range (ng/ml) | Optimum concentration (ng/ml) |
|---|---|---|
| For Conception of A Boy | | |
| Estradiol | 1-35 | 14.6 ± 1.46 |
| Estriol | 40-600 | 540 ± 54 |
| Estrone | 0.1-35 | 12.6 ± 1.26 |
| Testosterone | 1-25 | 13.6 ± 1.36 |
| Progesterone | 1-500 | 192 ± 19.2 |
| The concentrations the hormones should ensure that the [E − (T + P)]* value ranges from about 300 to about 1,500. | | |
| For Conception of A Girl | | |
| Estradiol | 1-20 | 11.7 ± 1.17 |
| Estriol | 80-500 | 265 ± 26.5 |
| Estrone | 1-20 | 8.1 ± 0.81 |
| Testosterone | 5-80 | 27.2 ± 2.72 |
| Progesterone | 100-1000 | 444 ± 44.4 |

The concentrations the hormones should ensure that the [E − (T + P)]* value ranges from about −10 to about −800.
*Although it should be the [E − (T + P + G)] value, as the contribution of hCG before pregnancy is negligible, G can be omitted here.

The hormones may be suspended in the pharmaceutical composition using a non-liquefying base containing purified water, and one or more of following components: propylene glycol, stearyl alcohol, white ceresin wax, mono- and di-glycerides, hypromellose 2208 (4000 cps), sodium lauryl sulfate, methylparaben, edetate di-sodium and tertiary-butylhydroquinone. The pharmaceutical composition preferably contains saline buffered at a physiological pH. The sex hormone composition of the pharmaceutical formulation is not limited to what is tabulated in Table 2. The pharmaceutical formulation may contain sex hormones in certain concentrations to be in accordance with the specific ranges taught in the present invention. For example, the formula (E+T)/(P+G) could be used to design pharmaceutical formulations for the conception of either a boy or a girl. Since contribution of hCG before pregnancy is negligible, G can be omitted. Accordingly, to select for a male conception, the sex hormones would be in such concentrations to give an (E+T)/P value ranging from about 300 to about 1,500. Similarly, to select for a female conception, the sex hormones would be in such concentrations to give an (E+T)/P value ranging from about −10 to about −800.

Therefore, the present invention provides a method of conceiving a baby of a desired gender in a female comprising the step of applying to the female a pharmaceutical formulation selected from the group consisting of: (i) a pharmaceutical formulation comprising about 1 ng/ml to about 35 ng/ml estradiol, about 40 ng/ml to about 600 ng/ml estriol, about 0.1 ng/ml to about 35 ng/ml estrone, about 1 ng/ml to about 25 ng/ml testosterone, about 1 ng/ml to about 500 ng/ml progesterone when the desired gender of the baby is male, wherein the [E−(T+P)] value ranges from about 300 to about 1,500, and (ii) a pharmaceutical formulation comprising about 1 ng/ml to about 20 ng/ml estradiol, about 80 ng/ml to about 500 ng/ml estriol, about 1 ng/ml to about 20 ng/ml estrone, about 5 ng/ml to about 80 ng/ml testosterone, about 100 ng/ml to about 1000 ng/ml progesterone when the desired gender of the baby is female, wherein the [E−(T+P)] value ranges from about −10 to about −800.

Sperm Sorting/Separation Based on Oxidizing/Reducing Environment

The composition of sex hormones and their ratios in two consecutive menstrual cycles differ, as described elsewhere herein. One cycle has more testosterone and progesterone as compared to all the three estrogens (estradiol, estrone and estriol) and this pattern reverses in the next cycle, as described elsewhere herein. These cycle to cycle variations impact the selective movement of sperm due to chemotactic forces, specifically oxidizing and reducing forces offered by individual hormones and signal transduction mechanisms inherent in sperm.

As described herein, the oxidizing/reducing properties of individual hormones control sperm selection. Hormones exhibit oxidizing or reducing properties depending upon the environment. In vivo, testosterone and progesterone show oxidizing properties whereas gonadotropins and estrogens show reducing properties. Out of these, hCG, which is only present after pregnancy, always demonstrates reducing properties regardless of the environmental conditions. As described herein, the overall oxidizing or reducing environment in the uterus, due to these hormones, imparts 'pulling' and/or 'pushing' forces on the sperm. In some embodiments, oxidizing conditions (higher T/E ratio) favor greater activation and movement of Y chromosome containing sperm, resulting in conception of a male fetus, and reducing conditions (lower T/E ratio) favor activation and movement of X chromosome containing sperm, resulting in conception of a female fetus. In some embodiments, one or more chemoattractants in the follicular fluid include progesterone, atrial natriuretic peptide, one or more odorants, bourgeonal, and/or the like.

In some embodiments, the oxidizing or reducing environment is dependent on a composition of the follicular fluid released in the uterus. Described herein are methods for sorting/separating X and Y chromosome containing sperm while avoiding potentially harmful side-effects as a result of typical sorting processes that use external forces to sort/separate sperm.

A method for sperm sorting includes: determining whether a female has regular menstrual cycles; recovering follicular fluid from two consecutive cycles; freezing the follicular fluid until use; acquiring mid-cycle urine samples for the two consecutive cycles in which follicular fluid was taken; and assaying the two urine samples to determine an oxidizing or reducing environment, as described elsewhere herein.

In some embodiments, the method further includes: providing a microfluidics channel; collecting a plurality of sperm from a donor; differentially dyeing or labeling the plurality of sperm based on the presence of either an X or a Y chromosome; applying the sperm to a central region of the microfluidics channel; applying diluted follicular fluid from a first cycle to a first end of the microfluidics channel; applying diluted follicular fluid from a second cycle to a second end of the microfluidics channel; and assessing movement of the plurality of sperm to the first and/or second end. Such movement may be recorded using fluorescence microscopy and/or time lapsed videography. As described herein, Y-containing sperm move towards the follicular fluid representing an oxidizing environment, while X-containing sperm move towards the follicular fluid representing a reducing environment.

Intrauterine Insemination Based on Oxidizing/Reducing Environment

A method for intrauterine or intracervical insemination includes: determining a gender specific compatibility of an ovum released in a menstrual cycle of a non-pregnant female; determining whether the fallopian tubes of the non-pregnant female are unobstructed; collecting semen from a male donor; cleaning a cervical area of the non-pregnant female; and when the fallopian tubes are unobstructed, dispensing the semen in the cervix or in the uterine cavity using a flexible elongate member. The method functions to allow the uterus time to select X or Y chromosome containing sperm depending upon the redox environment in the uterus.

In some embodiments, dispensing the semen in the cervix or uterine cavity is performed 1-3 times, at least three times, greater than three times, or substantially three times. For example, the inseminations are done at least three times in a cycle starting on the thirteenth, seventeenth, and twentieth day after the start of menstrual cycle.

In some embodiments, collecting the semen from the male donor occurs after 1-2, 2-5, or more than five days of abstinence from ejaculation.

In some embodiments, the method includes washing a plurality of sperm in the semen and concentrating the plurality of sperm in a small volume of media. In some embodiments, the media comprises phosphate buffered saline or a physiological saline buffer. In some embodiments, the volume is less than 1 mL, less than 0.5 mL, less than 0.25 mL, less than 0.1 mL. In some embodiments, the volume is 0.1-0.5 mL, 0.5-1 mL, or any range or subrange therebetween.

In some embodiments, cleaning the cervical area includes positioning a speculum in a vagina of the non-pregnant female.

In some embodiments, the elongate member includes a catheter.

The Examples illustrate embodiments of the invention and are not to be regarded as limiting.

Example 1

Post-Conception Tests Based on PTA Assay and FRAP Assay

Table 3 tabulates the results for post-conception tests conducted for 4,524 women during the period between 1999 and 2008, with an average observed accuracy of about 90%.

At the initial stage, i.e., from the years 1999 through mid-2003, urine samples were tested using sodium salicylate as the redox indicator combined with spectrophotometry (see Example 4). PITA test (see Example 4) was started in 2002. FRAP assay (see Example 5) has been conducted since 2008.

TABLE 3

| YEAR | Stage of pregnancy (wks) | Boys Observed | Boys Reported | Girls Observed | Girls Reported | Accuracy for Boys % | Accuracy for Girls % |
|---|---|---|---|---|---|---|---|
| 1999-2001 | 7 | 212 | 242 | 229 | 258 | 87.6 | 88.8 |
|  | 8 | 305 | 344 | 331 | 367 | 88.7 | 90.2 |
|  | 9 | 299 | 338 | 332 | 378 | 88.5 | 87.8 |
|  | 10 & up | 281 | 328 | 293 | 345 | 85.4 | 84.9 |
| 2002 | 6 | 22 | 29 | 23 | 25 | 75.9 | 92.0 |
|  | 7 | 21 | 31 | 18 | 19 | 67.7 | 94.7 |
|  | 8 | 32 | 36 | 19 | 21 | 88.9 | 90.5 |
|  | 9 | 17 | 21 | 20 | 22 | 81.0 | 90.9 |
|  | 10 & up | 46 | 54 | 26 | 31 | 85.2 | 83.9 |
| 2003 | 6 | 14 | 16 | 26 | 31 | 77.8 | 83.9 |
|  | 7 | 26 | 33 | 16 | 18 | 78.8 | 88.9 |
|  | 8 | 25 | 25 | 22 | 24 | 100.0 | 91.7 |
|  | 9 | 16 | 16 | 13 | 13 | 100.0 | 100.0 |
|  | 10 & up | 37 | 45 | 20 | 21 | 82.2 | 95.2 |
| 2004 | 6 | 16 | 19 | 13 | 15 | 84.2 | 86.7 |
|  | 7 | 26 | 35 | 19 | 22 | 74.3 | 86.4 |
|  | 8 | 22 | 29 | 22 | 24 | 75.9 | 91.7 |
|  | 9 | 9 | 12 | 12 | 14 | 75.0 | 85.7 |
|  | 10 & up | 16 | 21 | 26 | 31 | 76.2 | 83.9 |
| 2005 | 5 | 10 | 11 | 5 | 5 | 90.9 | 100.0 |
|  | 6 | 13 | 14 | 13 | 14 | 92.9 | 92.9 |
|  | 7 | 21 | 26 | 20 | 24 | 80.8 | 83.3 |
|  | 8 | 8 | 9 | 9 | 10 | 88.9 | 90.0 |
|  | 9 | 9 | 10 | 12 | 13 | 90.0 | 92.3 |
|  | 10 & up | 48 | 58 | 48 | 51 | 82.8 | 94.1 |
| 2006 | 5 | 22 | 23 | 20 | 22 | 95.7 | 90.9 |
|  | 6 | 30 | 33 | 24 | 25 | 90.9 | 96.0 |
|  | 7 | 13 | 13 | 15 | 15 | 100.0 | 100.0 |
|  | 8 | 15 | 15 | 11 | 13 | 100.0 | 84.6 |
|  | 9 | 8 | 8 | 8 | 9 | 100.0 | 88.9 |
|  | 10 & up | 26 | 28 | 39 | 41 | 92.9 | 95.1 |
| 2007 | 5 | 19 | 21 | 32 | 36 | 90.5 | 88.9 |
|  | 6 | 16 | 18 | 13 | 15 | 88.9 | 86.7 |
|  | 7 | 16 | 18 | 17 | 18 | 88.9 | 94.4 |

TABLE 3-continued

| YEAR | Stage of pregnancy (wks) | Boys Observed | Boys Reported | Girls Observed | Girls Reported | Accuracy for Boys % | Accuracy for Girls % |
|---|---|---|---|---|---|---|---|
|  | 8 | 20 | 24 | 15 | 15 | 83.3 | 100.0 |
|  | 9 | 12 | 13 | 12 | 14 | 92.3 | 85.7 |
|  | 10 & up | 39 | 42 | 45 | 48 | 92.9 | 93.8 |
| 2008 | 5 | 26 | 28 | 34 | 37 | 92.9 | 91.9 |
|  | 6 | 25 | 25 | 39 | 42 | 100.0 | 92.9 |
|  | 7 | 22 | 23 | 30 | 32 | 95.7 | 93.8 |
|  | 8 | 23 | 25 | 21 | 22 | 92.0 | 95.5 |
|  | 9 | 28 | 30 | 25 | 25 | 93.3 | 100.0 |
|  | 10 & up | 47 | 49 | 55 | 58 | 95.9 | 94.8 |
| TOTAL |  | 1,958 | 2,241 | 2,042 | 2,283 | 88% | 91.3% |
| Total Fetal Gender Predicted |  |  | 4,524 |  |  | Average Observed Accuracy: 90% |  |

From 1999 to 2001 we tested urine samples collected after 21 days past missed menstruation date. Since 2005, we have been testing urine samples collected as early as 1 day after missed menstruation, i.e., the 5th week of pregnancy.

If the urine samples were aged for a longer period of time, the accuracy of the present methods could approach 100%. However, from a clinical perspective, aging the urine samples for a long period of time is not applicable. Accordingly, techniques to accelerate the aging process by physical, chemical or biochemical means were developed.

Example 2

Post-Conception Tests Based on Calculation of (E+T)/(P+G)

The levels of the sex hormones were measured using commercially available ELISA kits (e.g., from Calbiotech Inc.).

Table 4 tabulates the results for post-conception tests conducted for 11 women based on calculating the value of (E+T)/(P+G), showing the different value ranges between women carrying a male fetus and women carrying a female fetus. For women carrying a male fetus, the ratio of (E+T)/(P+G) is greater than about 1.4. For women carrying a female fetus, the ratio of (E+T)/(P+G) is less than about 1.2.

TABLE 4

| Sample # | 1 | 2 | 3 | 4 | 5 | 6 | 14 | 15 | 16 | 17 | 18 |
|---|---|---|---|---|---|---|---|---|---|---|---|
| Gender | M | M | M | M | M | M | F | F | F | F | F |
| ng/ml | 4.4 | 6.1 | 14.4 | 21.9 | 11.6 | 22.9 | 19.6 | 6.8 | 8.0 | 68.0 | 33.6 |
| ng/ml | 1.0 | 3.5 | 1.3 | 20.9 | 28.8 | 32.1 | 20.4 | 4.4 | 8.5 | 10.4 | 14.9 |
| ng/ml | 42.2 | 167.7 | 388.0 | 1919.8 | 310.5 | 426.8 | 444.7 | 97.4 | 330.6 | 104.5 | 348.6 |
| ng/ml | 0.3 | 4.5 | 1.0 | 19.8 | 34.7 | 15.5 | 16.0 | 1.0 | 1.7 | 10.0 | 11.8 |
| ng/ml | 11.3 | 109.0 | 78.3 | 444.1 | 176.2 | 333.8 | 518.9 | 218.4 | 227.0 | 151.5 | 1106.3 |
| mIU/ml | 0.0 | 20.4 | 0.0 | 0.5 | 6.2 | 0.0 | 0.0 | 6.3 | 250.0 | 3.2 | 0.0 |
|  | 27.7 | 40.3 | 297.6 | 1494.0 | 180.1 | 117.7 | −57.4 | −128.7 | −144.1 | −97.8 | −764.7 |
|  | Oxidizing | Oxidizing | Oxidizing | Oxidizing | Oxidizing | Oxidizing | Reducing | Reducing | Reducing | Reducing | Reducing |
|  | Yellow Colloidal | Yellow Colloidal | Yellow Colloidal | Yellow Colloidal | Yellow Colloidal | Yellow Colloidal | Deep Blue Transparent | Deep Blue Transparent | Deep Blue Transparent | Deep Blue Transparent | Deep Blue Transparent |
|  | 4.2 | 1.4 | 5.2 | 4.5 | 2.1 | 1.5 | 1.0 | 0.5 | 0.7 | 1.2 | 0.4 |
|  | 3.15 | 0.76 |  |  |  |  |  |  |  |  |  |

The "Oxidizing minus Reducing" value is calculated as (Estradiol+Estriol+Estrone)−(Testosterone+Progesterone+hCG). The "Overall Redox" is oxidizing if "Oxidizing minus Reducing" value is positive; it is reducing if "Oxidizing minus Reducing" value is negative.

Example 3

Post-Conception Tests Based on the HORAC Value or Calculation of HORAC/(E/T)

The levels of the sex hormones were measured using commercially available ELISA kits (e.g., Calbiotech). The HORAC value was measured using HORAC Assay Kit from Oxford Biomedical Research.

Table 5 tabulates the results for post-conception tests conducted for 26 women based on the HORAC value or the value of HORAC/(E/T), showing the different value ranges between women carrying a male fetus and women carrying a female fetus.

about a week, and, if needed, a third test would be recommended to achieve an improved accuracy.

Similarly, other formulae like HORAC/(E−(T+P+G)) and HORAC/(E+T)/(P+G) can also be calculated from the same data provided numbers for P and G are known.

Example 4

Processing of Urine Samples for the PTA Assay

For the PTA assay, the urine samples were collected and processed as follows. Post-conception urine samples were collected from about 2,782 females at various time points of a pregnancy ranging from 4 days before missed menstruation to the 20th week of pregnancy. The customers were shipped a vial for urine sample collection with a boric acid tablet in the vial as a preservative. Customers were asked to collect urine voided during a resting period including early morning for at least two days. Customers who were working at night were asked to collect urine during day-time instead

TABLE 5

| Sample # | Gender | Testosterone ng/ml | Estradiol ng/ml | Estriol ng/ml | Estrone ng/ml | HORAC | HORAC Avg. | HORAC/ ((Total E)/T) | HORAC/((Total E)/T) AVG. |
|---|---|---|---|---|---|---|---|---|---|
| 1 | M | 4.44 | 1.01 | 42.16 | 0.32 | 2000 | | 204 | |
| 2 | M | 6.14 | 3.54 | 167.70 | 4.52 | 3000 | | 105 | |
| 3 | M | 14.45 | 1.32 | 388.04 | 0.95 | 2000 | | 74 | |
| 4 | M | 21.87 | 20.93 | 1919.75 | 19.85 | 4667 | | 52 | |
| 5 | M | 11.62 | 28.81 | 310.53 | 34.74 | 3995 | | 124 | |
| 6 | M | 22.93 | 32.13 | 426.79 | 15.48 | 2000 | | 97 | |
| 7 | M | 2.12 | 22.50 | 555.56 | 17.32 | 3000 | | 11 | |
| 8 | M | 0.90 | 24.66 | 536.74 | 14.48 | 3995 | | 6 | |
| 9 | M | 13.06 | 22.28 | 2009.26 | 14.17 | 2000 | | 13 | |
| 10 | M | 4.81 | 34.72 | 424.64 | 55.89 | 8000 | | 75 | |
| 11 | M | 2.69 | 4.24 | 146.17 | 7.31 | 3995 | | 68 | |
| 12 | M | 4.32 | 15.75 | 956.79 | 45.93 | 2000 | | 8 | |
| 27 | M | 61.74 | 21.81 | 436.12 | 13.23 | 1000 | 3204 | 131 | 74 |
| 13 | F | 16.67 | 21.08 | 473.45 | 14.36 | 1000 | | 33 | |
| 14 | F | 19.64 | 20.39 | 444.74 | 16.04 | 2000 | | 82 | |
| 15 | F | 6.77 | 4.41 | 97.37 | 1.04 | 8000 | | 527 | |
| 16 | F | 7.96 | 8.53 | 330.62 | 1.74 | 8000 | | 187 | |
| 17 | F | 68.03 | 10.35 | 104.55 | 10.02 | 7987 | | 4349 | |
| 18 | F | 33.60 | 14.87 | 348.56 | 11.77 | 8000 | | 716 | |
| 19 | F | 17.69 | 22.75 | 332.06 | 12.36 | 6667 | | 321 | |
| 20 | F | 13.80 | 20.20 | 216.51 | 18.13 | 7333 | | 397 | |
| 21 | F | 23.86 | 15.09 | 464.11 | 5.52 | 8000 | | 394 | |
| 22 | F | 49.49 | 27.49 | 1469.14 | 52.15 | 8000 | | 256 | |
| 23 | F | 13.33 | 12.54 | 433.97 | 11.99 | 8000 | | 233 | |
| 24 | F | 7.98 | 99.09 | 3486.73 | 172.31 | 7333 | | 16 | |
| 30 | F | 9.53 | 2.12 | 232.30 | 7.62 | 6000 | 6640 | 236 | 596 |

Except for three samples which had relatively high or low HORAC values (e.g., sample No. 10: 8000; sample No. 13: 1000; and sample No. 14: 2000), the majority of the samples from women carrying a male fetus had HORAC values less than about 5000; the majority of the samples from women carrying a female fetus had HORAC values greater than about 6000.

In general, for women carrying a male fetus, the ratio of HORAC/(E/T) is less than about 150. For women carrying a female fetus, the ratio of HORAC/(E/T) is greater than about 200.

Some values were out of the ranges of the majority of the samples, which cannot be explained at this time. For example, sample No. 17 had abnormally high value of HORAC/((Total E)/T) (4349). However, the majority of the samples had values falling within the ranges; the samples between women carrying a male fetus and women carrying a female fetus were statistically different. Accordingly, customers were generally asked to test their sample again after for three consecutive resting periods. The samples were returned to the clinic by mail which took from 2 to 5 days depending upon the distance. The delivery of the urine sample by mail provided a time period for sample aging. The urine sample may be further aged at room temperature for longer periods of time.

The urine was then processed as follows. 2 ml of the urine sample was passed through acidic alumina to eliminate significant amount of pigments and glucose. A C18 column was activated by methanol and pre-equilibrated with water. The cleared urine sample was then loaded on the C18 column to be subjected to solid phase extraction (SPE). After the urine sample passed through the C18 column, about 95% of sex hormones were retained on the column. The fraction of the urine sample that passed through or did not bind to the column was referred to as Fraction A. Fraction A was then treated with 50 ul of 10% $Na_2HPO_4$ and an excess amount of calcium phosphate (about 160 mg) to remove bilirubin, urobilinogen, porphyrins, and other pigments. 50 ul of saturated mercuric chloride was added to Fraction A to precipitate uric acid, ascorbic acid, creatine and some interfering proteins. 50 ul of 10% lead acetate solution was then added to Fraction A to remove creatine, some interfering proteins and bilirubin. 10 mg of barium chloride crystals was added to Fraction A to remove bilirubin, remaining interfering proteins and some interfering inorganic oxidants/reductants. The pH of Fraction A was then adjusted to 8.5 with 50 ul to 70 ul of 1 M sodium hydroxide, followed by centrifugation or filtration to remove the insoluble components.

In the PTA test, 20 mg of crystalline phosphotungstic acid was added to 0.75 ml of Fraction A, and the solution was kept below 21° C. for 12 hours. If the solution turned to a stable white fluorescent colloidal suspension after 12 hours, the urine sample was reported to be from a female exhibiting male gender related characteristics. If the solution initially formed white precipitates which later disappeared to result in a transparent solution, the urine sample was reported to be from a female exhibiting female gender related characteristics. Repeated analysis of the same urine sample aged for different periods of time improved the accuracy of the analytical results.

Example 5

Processing of Urine Samples for a FRAP Assay

For the FRAP assay, the urine samples were processed as follows. The urine samples were treated as above in Example 2; however, in this case the components that were retained on the C18 column were eluted and tested.

2 ml of the urine sample was passed through acidic alumina to eliminate significant amount of pigments and glucose. A C18 column was activated by methanol and pre-equilibrated with water. The cleared urine sample was then loaded on the C18 column After the urine sample passed through the C18 column, about 95% of sex hormones were retained on the column, which were than eluted with 1 ml of HPLC grade methanol and called Fraction B. Fraction B was diluted with 2 ml water. 2.5 ml of diluted Fraction B was mixed with 2.5 ml of 0.2 M phosphate buffer (pH 6.6) and 2.5 ml of 1% potassium ferricyanide. The mixture was incubated at 50° C. for 20 min and cooled to room temperature. The mixture was then mixed with 2.5 ml of 10% trichloroacetic acid and centrifuged at 6500 rpm for 10 min. The supernatant (2.5 ml) was mixed with 2.5 ml distilled water, before 0.5 ml of 0.1% ferric chloride was added. In this assay, the results were read within one minute after the addition of the ferric chloride, as the results were not stable at later time points.

If Fraction B turned to deep blue after the FRAP assay, the urine sample was reported to be exhibiting male gender related characteristics. If Fraction B turned to golden yellow, faint yellow or faint green after the FRAP assay, the urine sample was reported to be exhibiting female gender related characteristics. Repeated analysis of the same urine sample aged for different periods of time improved the accuracy of the analytical results.

If the same urine sample was analyzed by more than one type of assay, we have found that the accuracy of the results can approach 100%. For example, if the PTA test on Fraction A produced a stable white fluorescent colloidal suspension after 12 hrs, and the 1-RAP test on Fraction B resulted in a deep blue solution, it was almost 100% accurate that the urine sample was exhibiting male gender related characteristics. Similarly, if the PTA test on Fraction A produced a transparent solution after 12 hrs, and the FRAP test on Fraction B resulted in a solution with golden yellow, faint yellow or faint green in color, the accuracy was close to 100% that the urine sample was exhibiting female gender related characteristics.

Alternatively, the FRAP test can also be performed on Fraction A. When urine samples were aged for at least 3 months at room temperature, the accuracy of this method conducted was close to 100%.

Example 6

Redox Activity Assay with Sodium Salicylate

The urine samples were processed and assayed using sodium salicylate as follows. For post-conception urine sample assays, customers were asked to collect early morning urine samples on three consecutive mornings and drop them off at the clinic. All three samples from the same customer were studied separately and a report was issued after pooling the results. To process the urine sample, 4 ml of urine sample was treated with 20 mg of lead acetate for 30 minutes to precipitate interfering proteins. 1 ml of processed urine sample and 1 ml of 0.75 M hydrochloric acid were added to a 10 ml glass vial, before 1 ml of 1% sodium salicylate was added slowly to the vial which was gently shaken to mix the reagents. Controls for the test were also included where, instead of 1 ml of 1% sodium salicylate, 1 ml of distilled water was added to the vial. The reaction mixture was incubated at 50° C. for 2 hours and then cooled to room temperature. The absorbance of the reaction mixture at wavelengths between 470 nm to 550 nm was then measured against control in a spectrophotometer. When a peak was observed around wavelength 510 nm, a result of a male fetus was recorded for this sample. When a trough or a straight base line was observed around wavelength 510 nm, a result of a female fetus was recorded for this sample.

Example 7

FRAP Assay with Fe(III)-TPTZ

Fe(III)-TPTZ may also be used as the redox indicator for the FRAP assay. Under acidic conditions, Fe(III)-TPTZ complex can be reduced to Fe(II)-TPTZ. Fe(II)-TPTZ has intense blue color and can be monitored at wavelength 593 nm. FRAP working solution was freshly prepared by mixing 10 ml 300 mmol/l acetate buffer (pH 3.6), 1.0 ml 10 mmol/l TPTZ (2,4,6 tripyridyl-s-triazine) in 40 mmol/l HCl solution, and 1.0 ml 20 mmol/l $FeCl_3.6H_2O$ solution.

2 drops of processed urine sample were added to 0.5 ml FRAP working solution and the solution was incubated for 10 minutes. Under the harsh conditions of the FRAP assay, the urine from a female exhibiting male gender related characteristics has a comparatively higher overall reducing activity than urine from a female exhibiting female gender related characteristics. Accordingly, a urine sample from a female carrying a male fetus was able to reduce Fe(III)-TPTZ to Fe(II)-TPTZ, with the reaction mixture turned dark blue. In contrast, a urine sample from a female carrying a female fetus was not able to reduce Fe(III)-TPTZ, and thus, the reaction mixture remained yellow. When urine samples were aged for at least 3 months at room temperature, the accuracy of this method conducted on 161 urine samples was close to 100%. Among the 161 urine samples, 67 samples were from females carrying a male fetus; 94 samples were from females carrying a female fetus.

Example 8

Redox Activity Assay with Polyaniline-Coated Film

Polyaniline-coated film was prepared by chemical deposition of polyaniline on a transparent film of poly (ethylene terephthalate). 100 ml of the reaction mixture comprised 1 M sulfuric acid, 1 ml of aniline, 0.9 g of potassium iodate and 1 g of 5-sulfosalicyclic acid. U.S. Pat. No. 5,451,526. A deposition time of 2.5 hours at room temperature was used to produce the polyaniline film. The polyaniline coatings on both sides of the film were carefully washed to remove loose deposits. The film was dried, cut into small pieces (3 mm×2.0 cm), and stored in a clean container before use Immediately prior to use, the film was equilibrated in an acidic ferric chloride solution for 2 minutes to convert all the polyaniline to its emaraldine state, which is the oxidized state. 1.75 ml of urine was processed by passing through 160 mg of acidic alumina column, and transferred to a cuvette. The Polyaniline-coated film was carefully washed with deionized water and transferred to the cuvette containing aged or processed urine. The optical density of the liquid in the cuvette was read at wavelength 630 nm on a spectrophotometer. Alternatively, after washing, the film was dipped in the purified urine fraction for 1 second before being taken out for visual observation of its change in color. Under the mild condition of this assay, the aged and processed urine from a female carrying a female fetus has a comparatively higher overall reducing activity than urine from a female carrying a male fetus, and therefore, was able to reduce the emeraldine form of polyaniline (blue) to its more reduced leucoemeraldine state (off-white). An aged and processed urine sample from a female bearing a male fetus did not react with the emeraldine form of polyaniline (blue). As a result, the film remained blue in color. When fresh urine samples were used without processing, no difference could be observed in this test.

Example 9

Pre-Conception Assay

The overall redox activity of the body fluid during a menstrual cycle within which a female conceives is similar to the redox activity of her body fluid after conception. In other words, if conception occurs when midcycle urine sample of non-pregnant woman has an overall higher reducing activity, the process of conception "locks" this condition and a similar higher reducing activity is exhibited by urine sample from the same woman anytime after pregnancy. Namely, if her pre-conception body fluid has a comparatively higher overall reducing activity than that of the body fluid from a non-pregnant female carrying an ovum compatible with fertilization by an X chromosome-bearing sperm under the harsh condition (for example, in the FRAP assay), her ovum is compatible with fertilization by a Y chromosome-bearing sperm. Consistently, her post-conception urine sample would also have a higher overall reducing activity than that of urine from a female carrying a female fetus, which is correlated with a male fetus. Conversely, if her pre-conception urine sample has a higher overall oxidizing activity than that of urine from a non-pregnant female carrying an ovum compatible with fertilization by a Y chromosome-bearing sperm under harsh conditions, her ovum is compatible with fertilization by an X chromosome-bearing sperm. Likewise, her post-conception urine sample would also have a higher overall oxidizing activity than that of urine from a female carrying a male fetus, which is correlated with a female fetus.

The FRAP assay was used to test both pre-conception and post-conception urine samples obtained from the same customer. Pre-conception urine samples were collected during ovulation period for at least two consecutive months. Post-conception urine samples were collected on the first or second day of missed menstruation due to pregnancy. If the pre-conception samples indicated an alternating ovulation pattern, then the customer were advised as follows. If the customer desired a baby boy, she was advised to try conception in months when the ova being produced were compatible with fertilization by a Y chromosome-bearing sperm. If the customer desired a baby girl, she was advised to try conception in months when the ova being produced were compatible with fertilization by an X chromosome-bearing sperm (see Table 7 below).

Those customers whose urine samples indicated ova being released in two consecutive months had the same gender specific compatibilities were advised to collect more urine samples for additional tests. However, customers of this category did not wish to incur more costs and, therefore, did not continue after the initial tests.

Table 6 tabulates the results of pre-conception tests we conducted for 130 customers during the period between 2006 and August 2008.

TABLE 6

Number of customers who received the pre-conception test and later the post-conception test = 130

| Number of customers who desired a baby boy and tried conception according to our method = 71 | Number of customers who confirmed having a baby boy = 52 (Few did not call back*.) | Number of customers who desired a baby girl and tried conception according to our method = 59 | Number of customers who confirmed having a baby girl = 41 (Few did not call back*.) |
|---|---|---|---|
| Success rate for conception of baby boy = 73.2% | | Success rate for conception of baby girl = 69.5% | |
| Total success rate of pre-conception test = 71.3% | | | |

*As a policy, we never call a customer for a feedback due to confidentiality and privacy concerns.

Example 10

Pre-Conception Test Based on FRAP Assay and PTA Assay

Table 7 tabulates the results of pre-conception tests we conducted for 8 customers to assay the alternating ovulation pattern.

TABLE 7

| SAMPLE ID | DATE | FRAP TEST | 12 HR PTA TEST | STATUS REPORTED |
|---|---|---|---|---|
| K K | May 28, 2008 | BLUE | | Negative |
| | Jun. 28, 2008 | YELLOW | | Positive |
| | Jul. 28, 2008 | NS | | Assumed Negative |
| | Aug. 28, 2008 | NS | | Assumed Positive |
| | Missed Sep. 13, 2008 | | | Conception in Positive |
| | Tested Sep. 30, 2008 M | YELLOW | White Colloidal | DELIVERED M |
| D K | October 2007 | BLUE | | Negative |
| | November 2007 | YELLOW | | Positive |
| | December 2007 | NS | | Assumed Negative |
| | January 2008 | NS | | Assumed Positive |
| | February 2008 | NS | | Assumed Negative |
| | March 2008 | NS | | Assumed Positive |
| | April 2008 | NS | | Assumed Negative |
| | May 2008 | NS | | Assumed Positive |
| | Conceived June 2008 | | | Conception in Positive |
| | Tested Jun. 26, 2008 M | YELLOW | White Colloidal | DELIVERED M |
| P D | Aug. 3, 2008 | BLUE | | Negative |
| | Sep. 12, 2008 | YELLOW | | Positive |
| | Missed Sep. 26, 2008 | | | Conception in Positive |
| | Tested Oct. 8, 2008 M | YELLOW | White Colloidal | DELIVERED M |
| J B | Jun. 18, 2007 | YELLOW | | Positive |
| | Jul. 15, 2007 | BLUE | | Negative |
| | Aug. 12, 2007 | NS | | Assumed Positive |
| | Sep. 10, 2007 | NS | | Assumed Negative |
| | Oct. 7, 2007 | NS | | Assumed Positive |
| | Missed Oct. 25, 2007 | | | Conception in Positive |
| | Tested Oct. 29, 2007 M | YELLOW | White Colloidal | DELIVERED M |
| S M | Sep. 13, 2006 | YELLOW | | Positive |
| | Oct. 10, 2006 | BLUE | | Negative |
| | Missed Oct. 25, 2006 | | | Conception in Negative |
| | Tested Nov. 17, 2006 | BLUE | Transparent | DELIVERED F |
| J R | Aug. 22, 2008 | BLUE | | Negative |
| | Sep. 20, 2008 | YELLOW | | Positive |
| | Oct. 18, 2008 | NS | | Assumed Negative |
| | Nov. 16, 2008 | NS | | Assumed Positive |
| | Dec. 14, 2008 | NS | | Assumed Negative |
| | Missed Dec. 28, 2008 | | | Conception in Negative |
| | Tested Jan. 12, 2008 | BLUE | Transparent | DELIVERED F |
| R G | Jun. 8, 2006 | FAINT BLUE* | | Negative |
| | Jul. 5, 2006 | YELLOW | | Positive |
| | Aug. 4, 2006 | NS | | Assumed Negative |
| | Sep. 1, 2006 | NS | | Assumed Positive |
| | Sep. 27, 2006 | BLUE | | NEGATIVE |
| | Missed Oct. 10, 2006 | | | Conception in Negative |
| | Tested Nov. 12, 2006 | BLUE | Transparent | DELIVERED F |
| R T | May 5, 2007 | BLUE | | Negative |
| | Jun. 3, 2007 | YELLOW | | Positive |
| | Jul. 1, 2007 | NS | | Assumed Negative |
| | Jul. 30, 2007 | NS | | Assumed Positive |
| | Aug. 2, 2007 | NS | | Assumed Negative |
| | Missed Aug. 16, 2007 | | | Conception in Negative |
| | Tested Sep. 3, 2007 | YELLOW* | Transparent | REPORTED M, DELIVERED F |

All samples were tested +/−1 day near ovulation.
NS = Not studied.
*= Exception.

Pre-conception test was done for two consecutive months for every woman to assay the alternating pattern of ovulation. Almost 90% women had alternating reproductive environment.

Example 11

Pre-Conception Test Based on the HORAC Value and the Ratio of HORAC/(E/T)

Table 8 tabulates the results of pre-conception tests we conducted for 2 customers showing the HORAC value and the ratio of HORAC/(E/T).

TABLE 8

| Sample # | Gender | Testosterone ng/ml | Estradiol ng/ml | Estriol ng/ml | Estrone ng/ml | HORAC | HORAC/ ((Total E)/T) | HORAC/((Total E)/T) AVG. |
|---|---|---|---|---|---|---|---|---|
| 27 (1st pre-con test) | M | 7.13 | 1.56 | 117.46 | 0.39 | 2000 | 119 | 145 |
| 27 (2nd pre-con test) | | 6.77 | 1.88 | 116.03 | 0.60 | 3000 | 171 | |
| 30 (1st pre-con test) | F | 5.39 | 0.65 | 57.17 | 1.42 | 3995 | 364 | 694 |
| 30 (2nd pre-con test) | | 16.72 | 6.50 | 126.08 | 3.41 | 8333 | 1025 | |

Similarly, other formulae like HORAC/(E−(T+P+G)) and HORAC/(E+T)/(P+G) can also be calculated from the same data above provided numbers for P and G are also evaluated. Examples 12-16 illustrate various methods to process urine samples before assaying its overall redox activity.

Example 12

Processing of Urine Samples with Acidic Alumina, Calcium Chloride and Lead Acetate The pH of 3 ml urine sample was adjusted to 6.4 with 1 M HCl. The urine sample was then centrifuged to remove insoluble components. The supernatant was loaded to a column containing 200 mg acidic alumina to remove interfering agents. 50 ul of 10% $Na_2HPO_4$ and 80 mg of calcium chloride were then added to the cleared urine sample. The reaction mixture was incubated at room temperature for 5 minutes. 10 mg of lead acetate was added to the sample and the test tube was shaken until all lead acetate dissolved. After 5 minutes, the pH of the sample was adjusted to 8.5 with 2.5 M NaOH. The sample was then centrifuged at 12000 rpm for 2 minutes to remove insoluble components. The processed urine sample was then assayed using the PTA or FRAP assay (Examples 2 and 3). The FRAP assay worked better at a basic pH here.

Example 13

Processing of Urine Samples with Sulfuric Acid and Florisil 1 ml of fresh urine was added to a microcentrifuge tube and incubated on ice. Concentrated sulfuric acid was slowly added to the urine sample to reach its final concentration of 3 M in the urine sample. The microcentrifuge tube was inverted slowly several times and the mixture incubated at 37° C. for 24 hours. The sample was then centrifuged at 12000 rpm for 2 minutes before the supernatant was passed through Florisil to result in processed urine sample. 10 mg of crystalline phospho-24-tungstic acid was then added to 0.75 ml of this processed urine sample, and the PTA assay conducted (Example 2).

Example 14

Processing of Urine Samples with Ion Exchange Resins 2 ml of urine sample was adjusted to pH 5.3 with diluted glacial acetic acid. The urine sample was then centrifuged at 12000 rpm for 2 minutes. The supernatant was batch treated with 160 mg of well washed Dowex™ resins (Dow Chemical Company) IX 8-100 mesh Cl⁻ form ion exchange resin to remove porphyrins. This cleared urine sample was then processed as described in Example 8. The processed urine sample was assayed using the PTA or FRAP assay (Examples 2 and 3).

Example 15

Processing of Urine Samples with Nylon Filter

The pH of 2 ml of urine sample was adjusted to 4.0 with 1 M HCl, before the urine sample was centrifuged at 12000 rpm for 2 minutes. The supernatant was passed through 0.2 um Nylon filter to remove porphyrins. This cleared urine sample was then processed as described in Example 8. Example 16 Processing of Urine Samples with Acidic Alumina and Talc Example 16

Processing of Urine Samples with Acidic Alumina and Talc

In order to develop a home based gender test, 2 ml of urine sample was added to 200 mg of acidic alumina and talc, and the tube was shaken to ensure mixing. The sample was incubated at room temperature for 5 minutes, before the sample was filtered to obtain processed urine sample. The processed urine sample was assayed using the FRAP assay (Example 3).

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

What is claimed is:

1. A method for intrauterine or intracervical insemination of a non-pregnant female, the method including:
    determining a gender specific compatibility of an ovum released in a menstrual cycle of the non-pregnant female, wherein a net reducing activity of the menstrual cycle indicates a female gender specific compatibility of the ovum and a net oxidizing activity of the menstrual cycle indicates a male gender specific compatibility of the ovum; determining whether one or both fallopian tubes of the non-pregnant female are unobstructed to allow release of the ovum to increase fertilization potential;
    collecting semen from a male donor;
    separating the semen into X chromosome containing sperm and Y chromosome containing sperm according to chemotactic preferences by disposing the semen between a first and second separating fluid, wherein the X chromosome containing sperm are attracted to the first separating fluid and the Y chromosome containing sperm are attracted to the second separating fluid, wherein the first separating fluid is selected from the group consisting of a first follicular fluid sample, a first synthetic hormonal formulation, and a combination thereof, and wherein the second separating fluid is selected from the group consisting of a second follicular fluid sample, a second synthetic hormonal formulation, and a combination thereof;
    cleaning a cervical area of the non-pregnant female; and
    when one or both fallopian tubes are unobstructed, dispensing the semen in a cervix or a uterine cavity of the non-pregnant female using a flexible elongate member, wherein an X chromosome containing sperm subset of the semen traffics to the ovum when there is the net reducing activity of the menstrual cycle, and wherein a Y chromosome containing sperm subset of the semen traffics to the ovum when there is the net oxidizing activity of the menstrual cycle.

2. The method of claim 1, wherein the synthetic hormonal formulation comprises a mixture of sex hormones where ((E−(T+P)) is less than 1.0 to activate X chromosome containing sperm, wherein E is a level of estrogens in the formulation, T is a level of testosterone in the formulation, and P is a level of progesterone in the formulation.

3. The method of claim 1, wherein the synthetic hormonal formulation comprises a mixture of sex hormones where ((E−(T+P)) is greater than 1.0 to activate Y chromosome containing sperm, wherein E is a level of estrogens in the formulation, T is a level of testosterone in the formulation, and P is a level of progesterone in the formulation.

4. The method of claim 1, wherein collecting the semen from the male donor occurs after 2-5 days of abstinence from ejaculation.

5. The method of claim 1, further comprising washing a plurality of sperm in the semen and concentrating the plurality of sperm in a volume of media.

6. The method of claim 1, wherein cleaning the cervical area includes positioning a speculum in a vagina of the non-pregnant female.

7. The method of claim 1, wherein the method is performed in an absence of ovum or follicle-inducing chemicals.

8. The method of claim 1, further comprising collecting the first follicular fluid sample from the non-pregnant female during a first menstrual cycle and collecting the second follicular fluid sample from the non-pregnant female during a second menstrual cycle.

9. The method of claim 8, wherein the first menstrual cycle is consecutive with the second menstrual cycle.

10. The method of claim 1, wherein the X chromosome containing sperm and the Y chromosome sperm are differentially labeled with a label.

11. The method of claim 10, wherein the label comprises a fluorophore.

12. The method of claim 1, wherein dispensing the semen comprises only dispensing the X chromosome or Y chromosome containing sperm in the cervix or the uterine cavity of the non-pregnant female.

13. The method of claim 12, wherein the X chromosome containing sperm are dispensed when the gender specific compatibility of the ovum indicates the female gender, and the Y chromosome containing sperm are dispensed when the gender specific compatibility of the ovum indicates the male gender.

14. The method of claim 1, wherein dispensing the semen comprises dispensing the semen 2-4 times in the menstrual cycle.

15. The method of claim 14, wherein there is a time period of 2-4 days between each dispensing.

16. The method of claim 1, determining the gender specific compatibility of the ovum comprises:
    obtaining a urine sample fluid from the non-pregnant female;
    aging the urine sample at ambient temperature for at least about 2 days;
    passing the aged urine sample over a solid surface comprising antibodies specific to an estrogen, testosterone, progesterone, and human chorionic gonadotropin beta subunit (hCG-beta);
    contacting the solid surface with at least one redox indicator;
    detecting a net redox activity of the estrogen, testosterone, progesterone, and hCG-beta retained on the solid surface by the antibodies, wherein the net redox activity is detected by a change in a chemical property of the at least one redox indicator; and
    comparing the detected net redox activity to a known net redox activity of at least one standard.

17. The method of claim 16, wherein the at least one redox indicator is selected from the group consisting of: sodium salicylate, methylene blue, a heteropoly acid or its salt, a chromogenic chemical, a fluorophore, a redox sensitive polymer, and combinations thereof.

18. The method of claim 16, further comprising processing the urine sample prior to contacting the aged urine sample with the solid surface.

19. A method for intrauterine or intracervical insemination of a non-pregnant female, the method including:
    determining a gender specific compatibility of an ovum released in a menstrual cycle of the non-pregnant female, wherein a net reducing activity of the menstrual cycle indicates a female gender specific compatibility of the ovum and a net oxidizing activity of the menstrual cycle indicates a male gender specific compatibility of the ovum;

determining whether one or both fallopian tubes of the non-pregnant female are unobstructed to allow release of the ovum to increase fertilization potential;

collecting semen from a male donor;

separating the semen into X chromosome containing sperm and Y chromosome containing sperm by placing the semen in a central region of a microfluidics channel and providing a first separating fluid to a first end of the channel and a second separating fluid to a second end of the channel, wherein the X chromosome containing sperm are attracted to the first separating fluid and the Y chromosome containing sperm are attracted to the second separating fluid, wherein the first separating fluid is selected from the group consisting of a first follicular fluid sample, a first synthetic hormonal formulation, and a combination thereof, and wherein the second separating fluid is selected from the group consisting of a second follicular fluid sample, a second synthetic hormonal formulation, and a combination thereof;

cleaning a cervical area of the non-pregnant female; and when one or both fallopian tubes are unobstructed, dispensing the semen in a cervix or a uterine cavity of the non-pregnant female using a flexible elongate member, wherein an X chromosome containing sperm subset of the semen traffics to the ovum when there is the net reducing activity of the menstrual cycle, and wherein a Y chromosome containing sperm subset of the semen traffics to the ovum when there is the net oxidizing activity of the menstrual cycle.

\* \* \* \* \*